(12) United States Patent
Mauger et al.

(10) Patent No.: US 9,731,142 B2
(45) Date of Patent: Aug. 15, 2017

(54) MAGNETIC STIMULATION IN TISSUE-STIMULATING PROSTHESES

(71) Applicant: Cochlear Limited, Macquarie University (AU)

(72) Inventors: Stefan Mauger, Macleod (AU); Bill Metzenthen, Hampton (AU); John Heasman, Macquarie University (AU)

(73) Assignee: Cochlear Limited, Macquarie University, NSW (AU)

( * ) Notice: Subject to any disclaimer, the term of this patent is extended or adjusted under 35 U.S.C. 154(b) by 201 days.

(21) Appl. No.: 14/995,840

(22) Filed: Jan. 14, 2016

(65) Prior Publication Data
US 2016/0213943 A1    Jul. 28, 2016

Related U.S. Application Data

(60) Provisional application No. 62/106,309, filed on Jan. 22, 2015.

(51) Int. Cl.
| | |
|---|---|
| *A61N 1/00* | (2006.01) |
| *A61N 2/00* | (2006.01) |
| *A61N 2/02* | (2006.01) |
| *A61N 1/05* | (2006.01) |
| *A61N 1/36* | (2006.01) |

(52) U.S. Cl.
CPC .............. *A61N 2/002* (2013.01); *A61N 2/006* (2013.01); *A61N 2/02* (2013.01); *A61N 1/0541* (2013.01); *A61N 1/36032* (2013.01)

(58) Field of Classification Search
CPC ........ A61N 2/002; A61N 2/004; A61N 2/006; A61N 2/02; A61N 1/0541; A61N 1/36032
See application file for complete search history.

(56) References Cited

U.S. PATENT DOCUMENTS

2009/0254146 A1   10/2009   Bonmassar et al.
2015/0126802 A1*   5/2015   Lim ................... A61H 23/0236
                                                                  600/13

OTHER PUBLICATIONS

Prutchi, "Micromagnetic Stimulation as an Alternative to Electrical Stimulation for Implantable Devices? I don't think so . . . ," Published in Magnetic Stimulation, Neural Stimulation, Tech Talk on Apr. 20, 2013, 3 pages.

Bonmassar, et al., "Microscopic Magnetic Stimulation of Neural Tissue," Nature Communications, 3:921, DOI:10.1038/ncomms1914, Jun. 26, 2012, 10 pages.

Blake, et al., "Micro Magnetic Stimulation of the Feline Cochlea," 13th International Conference on Cochlear Implants and Other Implantable Auditory Technologies, Jun. 18-21, 2014, 1 page.

Gale, "Development of Innovative Technologies for Brain Stimulation: Going Microscopic to Overcome Earlier Limitations," Cleveland Clinic, Insights 2013, pp. 16-18.

Muggleton, et al., "Smaller magnets for smarter minds?," Trends in Cognitive Sciences, vol. 16, No. 9, Sep. 2012, pp. 452-453.

(Continued)

*Primary Examiner* — Robert N Wieland
(74) *Attorney, Agent, or Firm* — Edell, Shapiro & Finnan, LLC

(57) ABSTRACT

Presented herein are tissue-stimulating prostheses that deliver magnetic stimulation to a recipient. The magnetic stimulation is delivered to the nerve cells through the use of one or more implantable magnetic stimulation coils, such as stimulation coils and/or extra-cochlear stimulation coils.

20 Claims, 18 Drawing Sheets

(56) References Cited

OTHER PUBLICATIONS

Park, et al., "Activation of the central nervous system induced by micro-magnetic stimulation," Nature Communications, 4:2463, DOI:10.1038/ncomms3463, Sep. 13, 2013, 10 pages.

Cleveland Clinic, Office of Communications, "Innovative Biophysics Technology to Help Treat Neurological Diseases, A Good Idea Becomes a Great One through Collaboration," Notations Newsletter, vol. 16, No. 7, Jul. 2012, 2 pages.

* cited by examiner

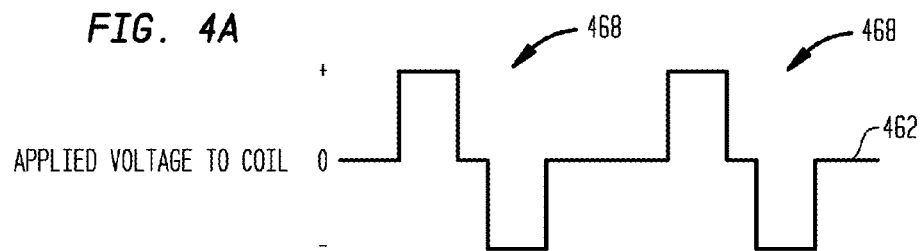
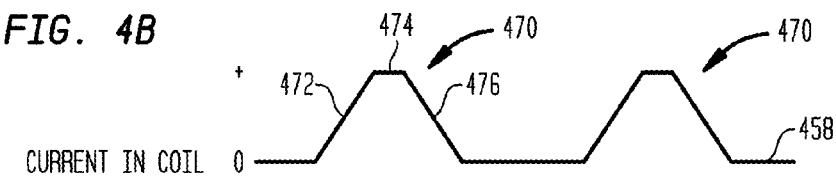
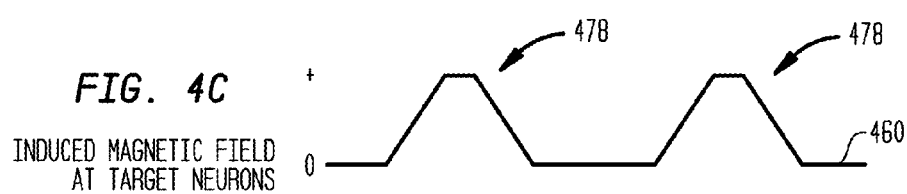
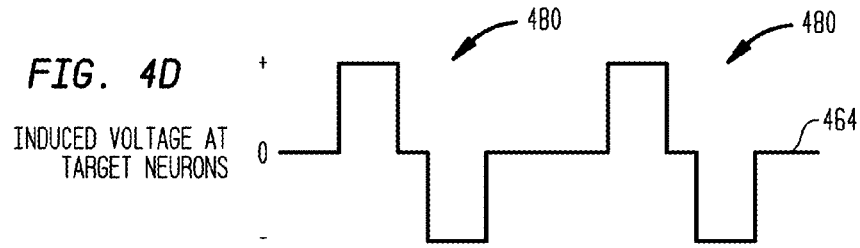
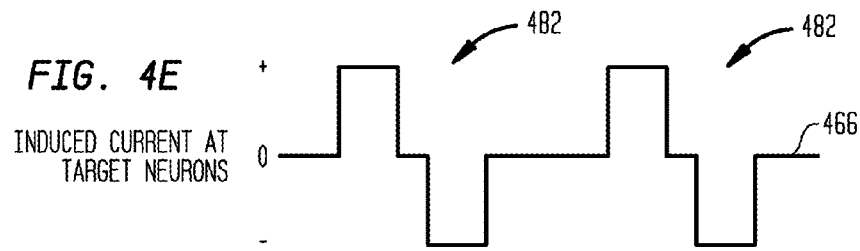

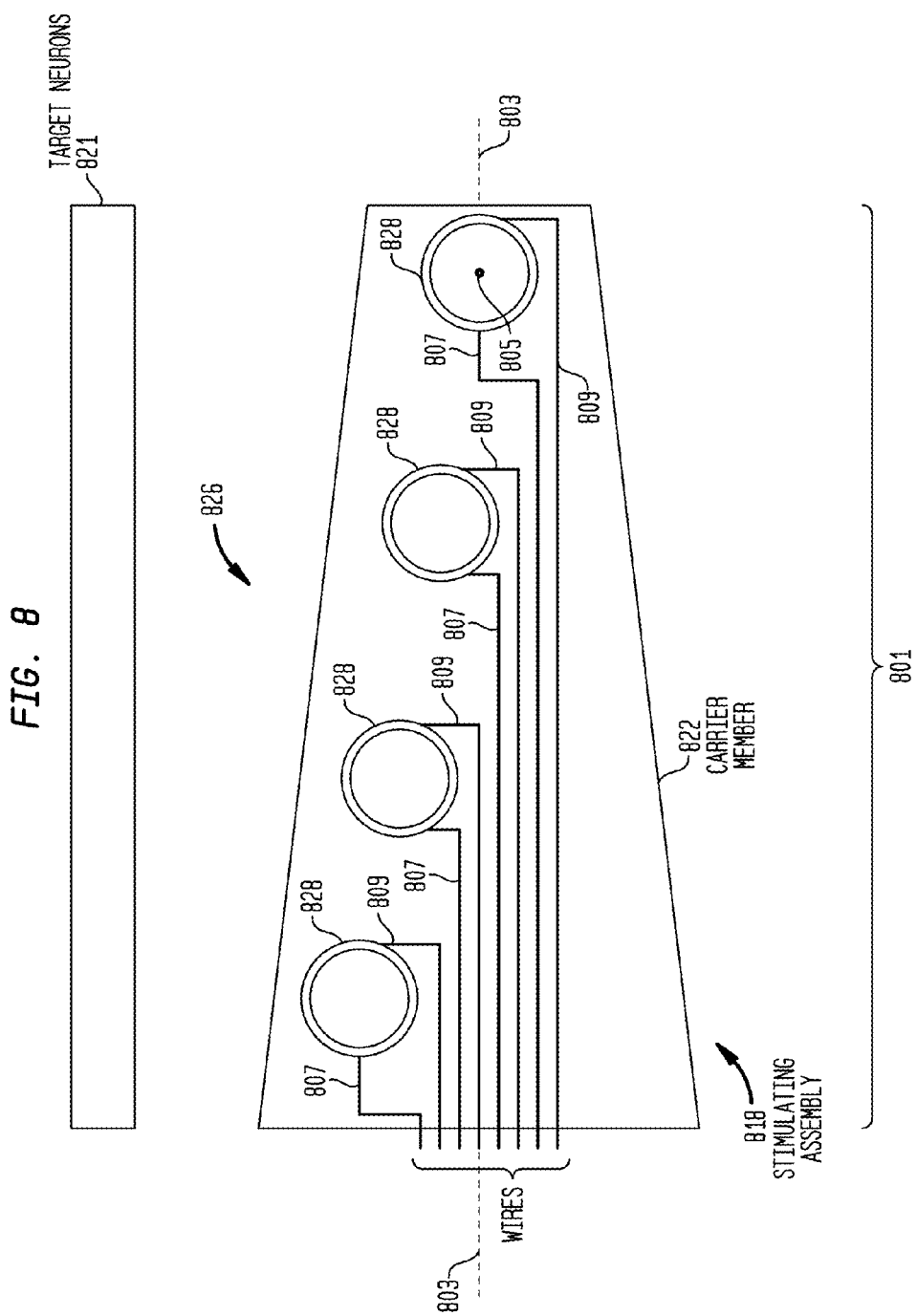

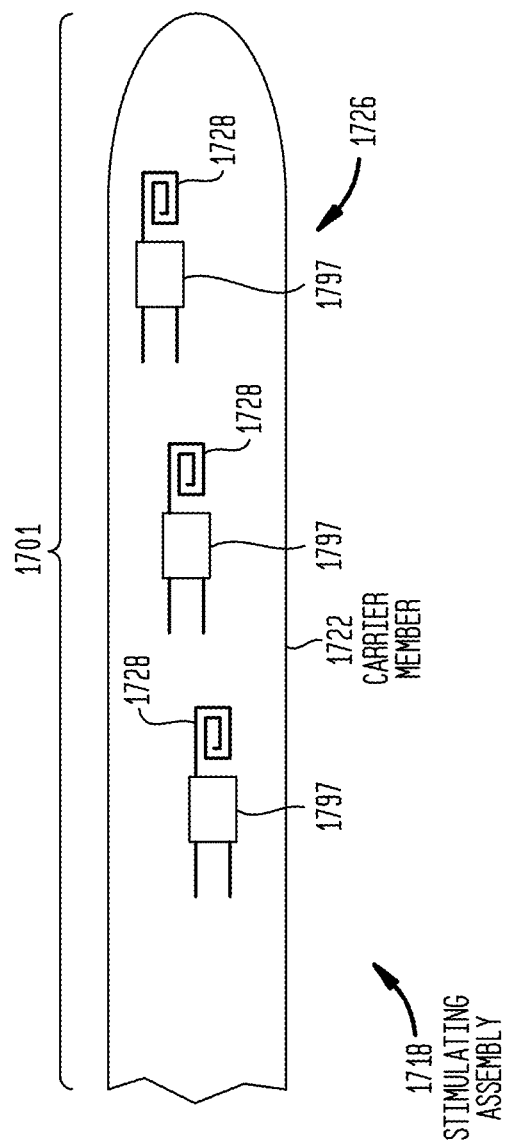

MAGNETIC STIMULATION IN TISSUE-STIMULATING PROSTHESES

CROSS-REFERENCE TO RELATED APPLICATIONS

This application claims priority to U.S. Provisional Application No. 62/106,309 entitled "Magnetic Stimulation in Tissue-Stimulating Prostheses," filed Jan. 22, 2015, the content of which is hereby incorporated by reference herein.

BACKGROUND

Field of the Invention

The present invention relates generally to tissue-stimulating prostheses.

Related Art

There are several types of medical devices that operate by delivering stimulation signals to the nerves, muscle or other tissue fibers of a recipient. These medical devices, referred to herein as tissue-stimulating prostheses, typically deliver stimulation to compensate for a deficiency in the recipient. For example, tissue-stimulating hearing prostheses, such as cochlear implants, are often proposed when a recipient experiences sensorineural hearing loss due to the absence or destruction of the cochlea hair cells, which transduce acoustic signals into nerve impulses. Auditory brainstem and/or midbrain stimulators are another type of tissue-stimulating hearing prostheses that might be proposed when a recipient experiences sensorineural hearing loss due to damage to the auditory nerve.

SUMMARY

In one aspect presented herein, a cochlear implant is provided. The cochlear implant comprises a substantially flexible stimulating assembly configured to be implanted into a recipient's cochlea adjacent to cochlea nerve cells, a plurality of stimulation coils positioned in the stimulating assembly, and a coil drive unit configured to apply drive signals to one or more of the stimulation coils to magnetically stimulate the cochlea nerve cells with the one or more stimulation coils.

In another aspect presented herein, a method is provided. The method comprises receiving a sound signal via one or more sound input elements of a tissue-stimulating auditory prosthesis, generating a plurality of drive signals based on the sound signal, and delivering the drive signals to one or more stimulation coils positioned in proximity to a recipient's nerve cells to induce, via the one or more stimulation coils, current at the nerve cells that is representative of the sound signal.

In other aspect, a hearing prosthesis is provided. The hearing prosthesis comprises: a sound input element configured to receive a sound signal; a coil drive unit configured to generate a plurality of drive signals based on the sound signal; and a plurality of stimulation coils configured to induce, at nerve cells of a recipient, current based on the drive signals, wherein the current is configured to evoke perception of the sound signal by the recipient.

BRIEF DESCRIPTION OF THE DRAWINGS

Embodiments of the present invention are described herein in conjunction with the accompanying drawings, in which:

FIG. 4A is a diagram illustrating voltage applied to a stimulation coil in accordance with embodiments presented herein;

FIG. 4B is a diagram illustrating coil current induced by application of the voltage of FIG. 4A of a stimulation coil;

FIG. 4C is a diagram illustrating a magnetic field induced by the coil current of FIG. 4B;

FIG. 4D is a diagram illustrating voltage induced at target neurons by the magnetic field of FIG. 4C;

FIG. 4E is a diagram illustrating current induced at target neurons by the magnetic field of FIG. 4C;

FIG. 8 is a cross-sectional side view of a section of another stimulating assembly that includes an array of stimulation coils in accordance with embodiments presented herein;

FIG. 17 is a cross-sectional side view of a section of an intra-cochlear stimulating assembly in accordance with embodiments presented herein.

DETAILED DESCRIPTION

Presented herein are tissue-stimulating prostheses that deliver magnetic stimulation to a recipient. As used herein, magnetic stimulation refers to the induced (i.e., non-direct) activation of nerve cells in response to the application/delivery of a magnetic field to the nerve cells. The magnetic field is applied to the nerve cells through the use of one or more implantable magnetic stimulation coils, such as intra-cochlear stimulation coils and/or extra-cochlear stimulation coils.

As noted, there are several types of tissue-stimulating prostheses that deliver stimulation to compensate for a deficiency in the recipient. Merely for ease of illustration, the magnetic stimulation techniques presented herein are primarily described with reference to one type of tissue-stimulating prosthesis, namely a cochlear implant. However, it is to be appreciated that the techniques presented herein may be used with other tissue-stimulating prostheses including, for example, auditory brainstem stimulators, auditory midbrain implants, implantable pacemakers, defibrillators, functional electrical stimulation devices, pain relief stimulators, visual prostheses, other neural or neuromuscular stimulators, etc.

Figure 1:
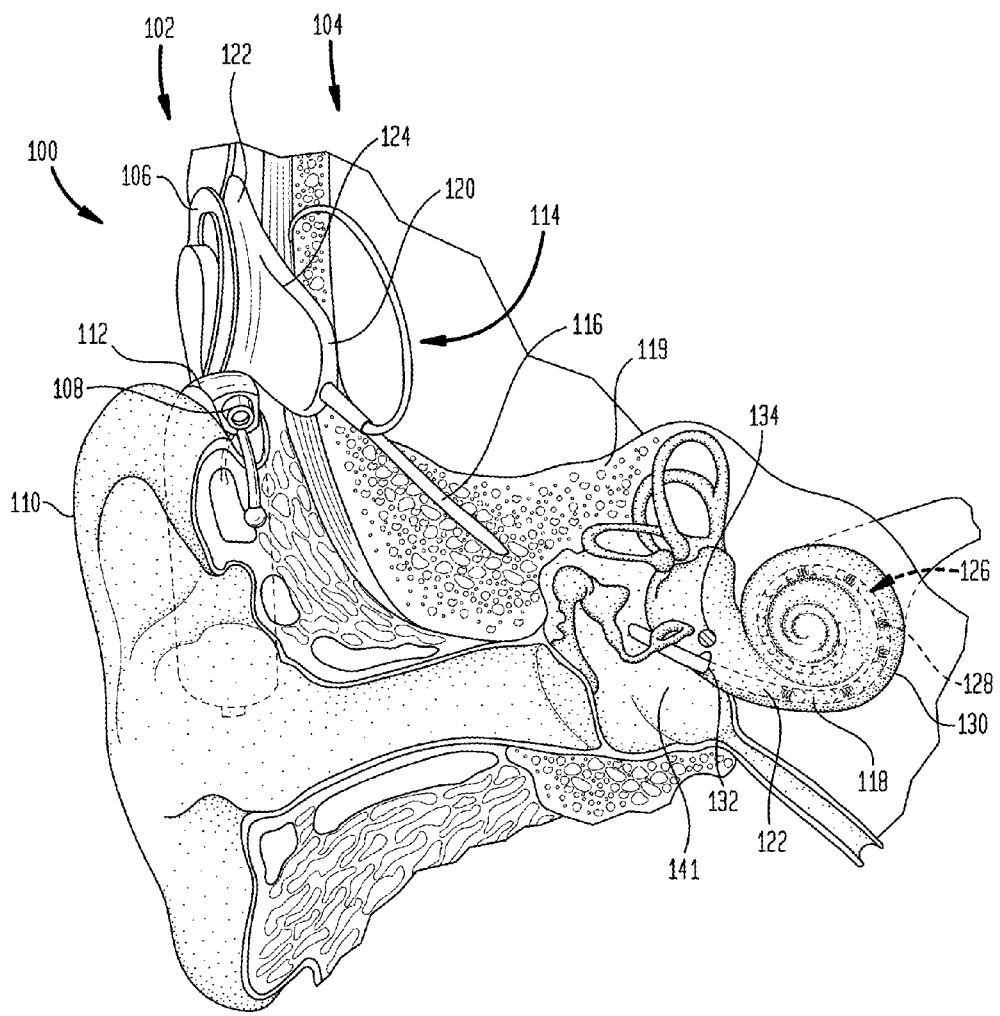
FIG. 1 is a schematic diagram of a cochlear implant configured to deliver magnetic stimulation to a recipient in accordance with embodiments presented herein.

FIG. 1 illustrates an exemplary cochlear implant 100 configured to deliver magnetic stimulation to a recipient in accordance with embodiments of the present invention. In the illustrative arrangement of FIG. 1, the cochlear implant 100 includes an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound and a sound processing unit 112. The sound processing unit 112 includes, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a wireless connection or a cable (not shown in FIG. 1).

The implantable component 104 comprises an implant body 114, a lead region 116, and an elongate intra-cochlear stimulating assembly 118. The stimulating assembly 118 includes a carrier member 122 and has configuration so as to be at least partially implanted in the recipient's cochlea. That is, the stimulating assembly 118 is has a flexibility such that, when inserted into the cochlea 130, the stimulating assembly 118 will assume a curved shape that generally follows the spiral shape of the cochlea. More specifically, the stimulating assembly 118 may be a perimodiolar stimulating assembly or a non-perimodiolar stimulating assembly. A perimodiolar stimulating assembly is a stimulating assembly that is configured to adopt a curved configuration during and/or after implantation into the recipient's cochlea so as to have at least the distal section positioned close to the wall of the recipient's modiolus (i.e., close to the modiolar wall). One type of non-perimodiolar stimulating assembly is a lateral stimulating assembly that is configured to be implanted so as to be positioned along the lateral wall of the recipient's scala tympani (i.e., the wall that is opposite the modiolar wall). Another type of non-perimodiolar stimulating assembly is a mid-scala stimulating assembly which assumes a mid-scala position during or following implantation (i.e., positioned approximately midway between the modiolar wall and the lateral wall).

The implant body 114 comprises a coil drive unit 120, an internal/implantable coil 122, and an internal receiver/transceiver unit 124, sometimes referred to herein as transceiver unit 124. The transceiver unit 124 is connected to the internal coil 122 and, generally, a magnet (not shown) fixed relative to the implantable coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 is positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

The cochlea 130 forms part of the recipient's auditory system. In general, the human auditory system is composed of many structural components, some of which are connected extensively by bundles of nerve cells (neurons). Each nerve cell has a cell membrane which acts as a barrier to prevent intercellular fluid from mixing with extracellular fluid. The intercellular and extracellular fluids have different concentrations of ions, which leads to a difference in charge between the fluids. This difference in charge across the cell membrane is referred to herein as the membrane potential (Vm) of the nerve cell. Nerve cells use membrane potentials to transmit signals between different parts of the auditory system.

More specifically, in nerve cells that are at rest (i.e., not transmitting a nerve signal), the nerve cell membranes have a "resting" potential. Upon receipt of a stimulus, the electrical properties of a nerve cell membranes are subjected to abrupt changes, referred to herein as a nerve action potential, or simply action potential. The action potential, which is also sometimes referred to as the "firing" of the nerve cell, represents the transient depolarization and repolarization of the nerve cell membrane. The action potential causes electrical signal transmission along the conductive core (axon) of a nerve cell. Signals are then transmitted along a group of nerve cells via propagation of such action potentials.

In normal hearing, the cochlea of a recipient includes thousands of hair cells that detect motion of the cochlea fluid. Movement of the hair cells results in the release of nerve impulses that cause action potentials within nerve cells, resulting in the perception of a sound. In cochlear implant recipients, the cochlea hair cells are generally missing and/or damaged. As such, most conventional cochlear implants use electrical stimulating contacts to directly deliver stimulation current to the nerve cells. The stimulation current delivered to the nerve cells causes action potentials within the nerve cells, resulting in the perception of a sound.

A problem associated with conventional cochlear implants and other tissue-stimulating prostheses is that the stimulating elements (e.g., electrical stimulating contacts) are exposed to the recipient's body tissue/fluid. That is, a direct interface is needed between the electrical stimulating contacts and the recipient's nerve cells so that current can flow from the contacts into the tissue. The need to expose the electrical stimulating contacts to the recipient's body tissue/fluid creates several difficulties/issues, including material biocompatibility, long term stability, charge injection limits, tissue safety limits, impedance changes, constant (DC) current, symmetric charge recovery, tissue encapsulation, etc. These issues remain a significant limitation in the design of cochlear implants and other tissue-stimulating prostheses. As such, presented herein are techniques that enable stimulation to be delivered to a recipient without a direct interface between the stimulating elements and the recipient's body tissue/fluid. More specifically, as shown in FIG. 1, the stimulating assembly 118 includes a plurality of stimulation coils 128 that are fully encapsulated within a carrier member 122. As such, the stimulation coils 128 are not exposed to the recipient's body tissue/fluid.

As used herein, stimulation coils are formed by a plurality of loops of material (e.g., wire) and have a size and configuration so as to be implanted within a recipient adjacent to a localized target population of nerve cells that form part of a target system. In general, stimulation coils have a size and configuration such that a plurality of the stimulation coils are implanted adjacent to a target system in a manner that enables the use of different stimulation coils to activate, partially or fully, different localized populations of nerve cells within the target system. For example, in the context of cochlear implant 100, and cochlear implants in general, stimulation coils 128 have a size and configuration such that a plurality of the coils can be implanted within cochlea 130 adjacent to the recipient's cochlea nerve cells (target system). In this way, the stimulation coils 128 can selectively activate different populations of cochlea nerve cells.

The stimulation coils 128 of FIG. 1 collectively form a coil array 126. For ease of illustration, only a few stimulation coils 128 are shown in FIG. 1. As described further below, the stimulating assembly 128 may also comprise one or more stimulating contacts, such as electrical contacts and/or optical contacts, which are not shown in FIG. 1.

As noted, the stimulating assembly 118 is configured to, when implanted, assume a curved shaped that generally follows the spiral shape of the cochlea. As such, the stimulation coils 128 are arranged (i.e., sized, shaped, positioned, oriented, etc.) such that stimulating assembly 118 can flex/bend to assume the curved shape upon implantation.

Stimulating assembly 118 extends through an opening in the cochlea 130 (e.g., cochleostomy 132, the round window 134, etc.) and has a proximal end connected to coil drive unit 120 via lead region 116 that extends through mastoid bone 119. Lead region 116 couples the stimulating assembly 118 to implant body 114 and, more particularly, coil drive unit 120. In operation, the coil drive unit 120 is configured to deliver/apply drive signals to the stimulation coils 128. As described further below, the coil drive unit 120 is configured to apply voltage and/or current to the stimulation coils 128. As a result of the applied voltage or current, a coil current will flow through a corresponding stimulation coil 128 which, in turn, generates a magnetic field in proximity to the coil. The magnetic field induces current within the recipient's cochlea nerve cells, thereby causing the firing of those nerve cells and perception of a sound.

The magnetic stimulation techniques presented herein enable current to be induced in a recipient's tissue without direct tissue/fluid contact and, accordingly, many of the above noted problems with electrical stimulating contacts are eliminated. Additionally, the magnetic stimulation techniques presented herein provide a number of manufacturing and safety benefits over tissue-stimulating prostheses that utilize electrical stimulating contacts. For example, the manufacturing of tissue-stimulating prostheses with stimulation coils is simpler since the whole arrangement of stimulation coils can be encapsulated. With a fully encapsulated device, there is no longer a need to ablate silicone from electrical stimulating contacts. Manufacturing quality is also improved since coils are able to be tested individually prior to encapsulation. Also, since the current within the tissue is induced, there is no grounding, shorting or current retrieval needed. In fact, the magnetic field inherently reverses the induced current by returning to the resting state. Local and novel current directions can be achieved at the neurons and the activation of multiple stimulation coils together could create new (narrow or broad) activation patterns. Hardware is also more highly tuned/controlled, since inductive coupling with the tissue would be expected to be more consistent between recipients than the complex electrical stimulating contact-body (electrode-tissue) interactions which can generate a large range of impedances with electrical stimulation. Furthermore, the magnetic field from a stimulation coil is essentially that of a dipole and falls off as the inverse cube of the distance from the coil, i.e. significantly faster than the inverse square relationship which applies to a (monopolar) electrical stimulating contact. In this respect, the induced currents due to a stimulation coil can be more localized than those from a conventional electrical stimulating contact.

FIG. 1 illustrates an example in which cochlear implant 100 includes an external component 102 with an external sound processing unit 112. It is to be appreciated that the use of an external component is merely illustrative and that the techniques presented herein may be used in arrangements having an implanted sound processor (e.g., totally implantable cochlear implants). It is also to be appreciated that the individual components referenced herein, e.g., sound input element 108 and the sound processor in sound processing unit 112, may be distributed across more than one tissue-stimulating prosthesis, e.g., two cochlear implants 100, and indeed across more than one type of device, e.g., cochlear implant 100 and a consumer electronic device or a remote control of the cochlear implant 100.

Figure 2:
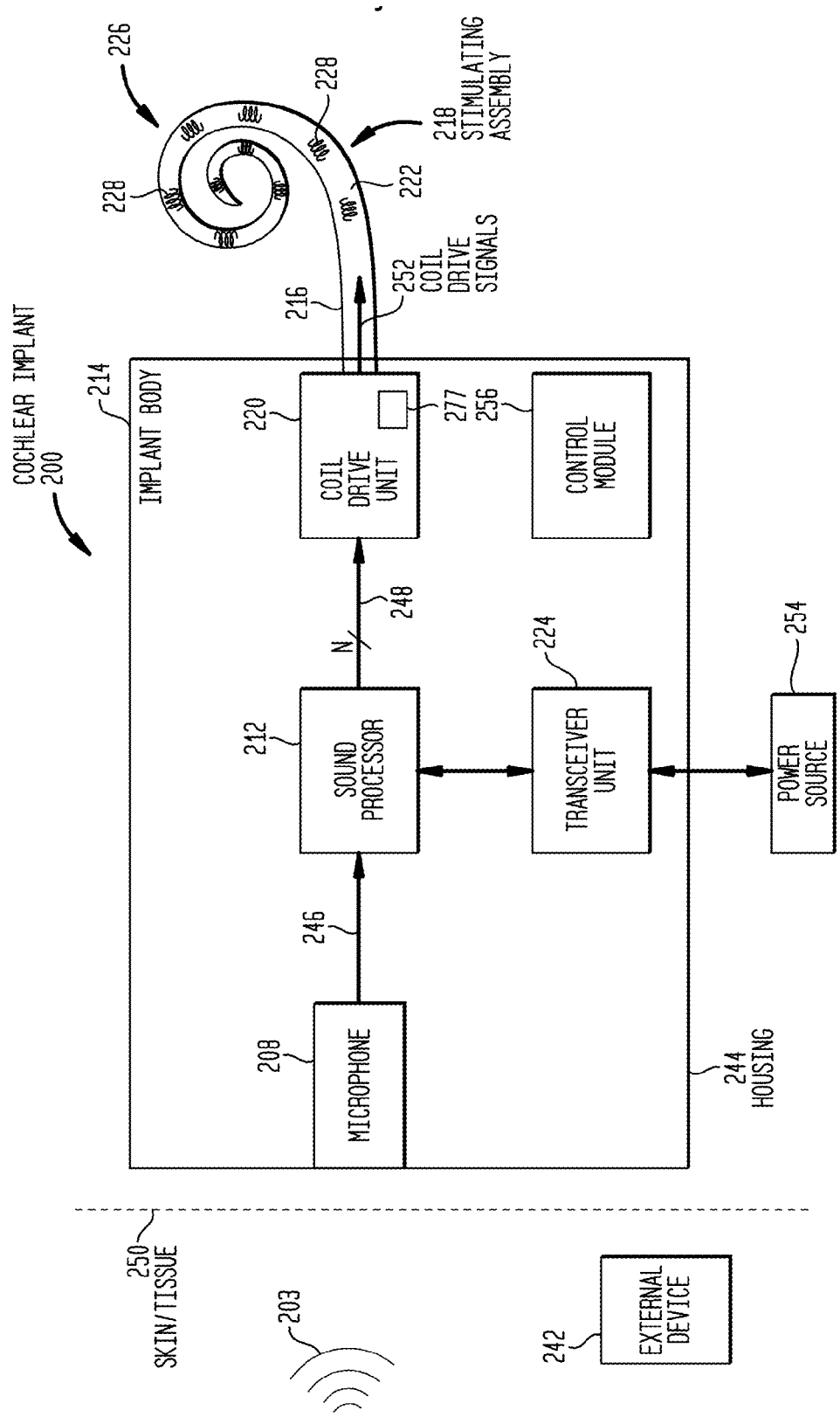
FIG. 2 is a block diagram of a totally implantable cochlear implant configured to deliver magnetic stimulation to a recipient in accordance with embodiments presented herein.

For example, FIG. 2 is a functional block diagram of one arrangement for a totally implantable cochlear implant 200 that is configured to deliver magnetic stimulation to a recipient in accordance with embodiments presented herein. That is, FIG. 2 illustrates an arrangement in which all components of cochlear implant 200 are configured to be implanted under skin/tissue 250 of a recipient. Because all components of cochlear implant 200 are implantable, cochlear implant 200 operates, for at least a finite period of time, without the need of an external device. However, an external device 242 can be used to, for example, charge an implantable power source of cochlear implant 200, to supplement the performance of the implanted microphone, as a back-up power source when the implantable power source no longer functions, etc. As such, external device 242 may be a dedicated charger, a supplemental sound input element, a supplemental sound processor, etc.

Cochlear implant 200 includes an implant body 214 having a hermetically sealed, biocompatible housing 244. Disposed in implant body 214 is a microphone 208 that is configured to sense sound signals 203. Microphone 208 may include one or more components to pre-process the microphone output. As an alternative, the microphone and other aspects of the system can be included in an upgrade or tethered module as opposed to in a unitary body as shown in FIG. 2.

An elongate intra-cochlear stimulating assembly 218 is connected to the implant body 214 via a lead region 216. Elongate stimulating assembly 218, which is at least partially implanted in a recipient's cochlea (not shown in FIG. 2) comprises a carrier member 222 formed from, for example, an elastomer material. Disposed in carrier member 222 is a plurality of stimulation coils 228. The stimulation coils 228 collectively form a coil array 226. For ease of illustration, only several stimulation coils 228 are shown in FIG. 2.

In the embodiment of FIG. 2, electrical signals 246 representing sound signals 203 detected by microphone 208 are provided from the microphone to a sound processor 212. Sound processor 212 implements one or more sound processing and/or coding strategies to convert the pre-processed microphone output (electrical signals 246) into data signals 248 for use by coil driver unit 220. Coil drive unit 220 utilizes the data signals 248 to generate coil drive signals 252 for delivery to the plurality of stimulation coils 228. As described further below, the coil drive signals 252 may be voltages that are applied to the stimulation coils 228 to induce a current to flow within the stimulation coils 228. Alternatively, the coil drive signals 252 may be current that is passed through the stimulation coil.

The stimulation coils 228 are connected to two (2) wires, namely a source/drive wire and a ground/return wire. For ease of reference, the drive wires and return wires have been omitted from FIG. 2. The drive wires connect a first end of each of the stimulation coils 228 to the coil drive unit 220, while the return wires connect a second end of each of the stimulation coils 228 to the coil drive unit 220. Voltage (or current) stimuli are applied to the stimulation coils 228 via the drive wires and the induced or applied current passes through return wires to the return(s) of the coil drive unit.

The use of "source" or "drive" and "ground" or "return" to refer to the wires connected to the first and second ends, respectively, of the stimulation coils is merely for ease of reference and does not limit the function of the wires. For example, in certain examples, voltage and/or current may be applied to the stimulation coils 228 from either of the ends of the stimulation coils to reverse the flow of current within a coil. As such, certain embodiments enable the use of the "return" wires to apply signals to the stimulation coils 228 and the use of the drive wires for return of current to the coil drive unit 220. To enable the reverse flow of current, a switching circuit 277 is connected to the drive wires and the return wires. The switching circuit 277 is configured to connect the second ends of the stimulation coils 228 to the coil drive unit 220 for supply of current and to connect the first ends of the stimulation coils to the coil drive unit 220 for the return of current. FIG. 2 illustrates the switching circuit 277 as part of the coil drive unit 220. It is to be appreciated that this location for the switching circuit 277 is merely illustrative.

As described further below, stimulating assemblies in accordance with embodiments presented herein may include different numbers of stimulation coils in various arrangements and may also comprise one or more stimulating contacts, such as electrical contacts and/or optical contacts. In embodiments in which a stimulating assembly includes stimulation coils and stimulating contacts, the coil drive unit also includes the circuitry to drive the stimulating contacts.

Cochlear implant 200 also includes a rechargeable power source 254 (e.g., one more rechargeable batteries). Power is received from an external device, such as external device 242, and is stored by power source 254. The power is distributed to the other components of cochlear implant 200 as needed for operation. For ease of illustration, implant body 214 and power source 254 are shown separate. However, power source 254 can alternatively be integrated into a hermetically sealed housing 244 or may form part of a separate module coupled to body 214.

Implant body 214 further comprises a control module 256 that includes various components for controlling the operation of cochlear implant 200. For example, control module 256 controls the delivery of power from power source 254 to other components of cochlear implant 200. Similar to the embodiment of FIG. 1, cochlear implant 200 further comprises a receiver or transceiver unit that permits the cochlear implant to receive and/or transmit signals to an external device. For ease of illustration, cochlear implant 200 is shown having a transceiver unit 224 in implant body 214. In alternative arrangements, cochlear implant 200 includes a receiver or transceiver unit which is implanted elsewhere in the recipient outside of implant body 114.

Transceiver unit 224 is configured to transcutaneously receive power and/or data from external device 242. As used herein, transceiver unit 224 refers to any collection of one or more implanted components which form part of a transcutaneous energy transfer system. Further, transceiver unit 224 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data from external device 242 to cochlear implant 200.

Transceiver unit 224 receives power and/or data from external device 242. In the illustrative arrangement of FIG. 2, external device 242 comprises a power source (not shown) disposed in a Behind-The-Ear (BTE) unit. External device 242 also includes components that form a transcutaneous energy transfer link with transceiver unit 224 to transfer the power and/or data to cochlear implant 200. The external device 242 shown in FIG. 2 is merely illustrative, and other external devices can be alternatively used.

Figure 3A:
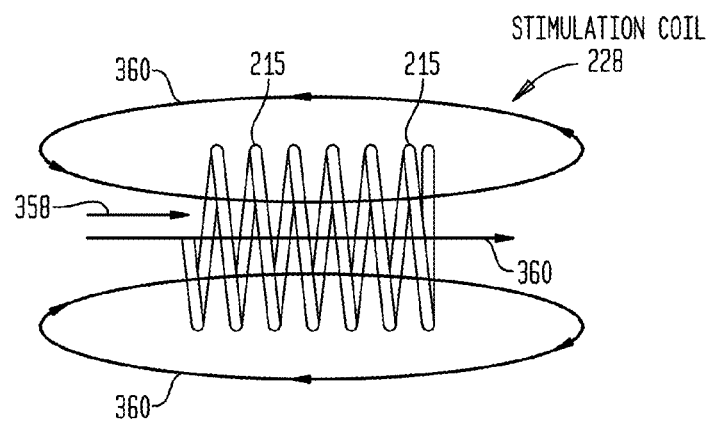
FIG. 3A is a side view of a stimulation coil in accordance with embodiments presented herein.
Figure 3B:
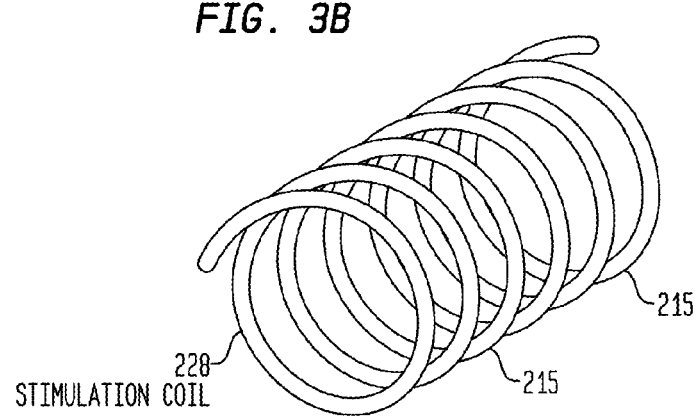
FIG. 3B is a perspective view of the stimulation coil of FIG. 3A.

As noted above, embodiments of the present invention are directed to tissue-stimulating prosthesis, such as cochlear implants, that utilize stimulation coils to deliver magnetic stimulation to a recipient. FIGS. 3A and 3B are side and perspective views, respectively, of a stimulation coil 228 from FIG. 2. As shown, stimulation coil 228 is formed by a plurality of loops 215 of wire.

Magnetic stimulation of a recipient operates by causing current to flow (i.e., though direct application of current or induced current through application of voltage) within an implanted stimulation coil. For example, coil drive signals (not shown in FIGS. 3A and 3B) are delivered to the stimulation coil 228 so as to cause a current to flow through the stimulation coil, referred to herein as a "coil current." The general direction of the coil current is shown in FIG. 3A by arrow 358. When current is passed through stimulation coil 228, a magnetic field, illustrated by lines 360, is generated. As shown, the magnetic field 360 flows through and around the stimulation coil 228 (i.e., the generated magnetic field 360 extends beyond the magnetic stimulation coil 228 itself).

In operation, the stimulation coil 228 is implanted so as to be positioned in proximity to a recipient's tissue that includes nerve cells (neurons). Therefore, when the stimulation coil 228 is implanted in a recipient, the magnetic field 360 induced by the flow of current through stimulation coil 228 will also pass through the recipient's tissue positioned proximate to the coil. A constant magnetic field 360 flowing through the proximate tissue does not affect the nerve cells therein. However, changes in the magnetic field 360 flowing through the tissue will induce current to flow in the tissue such that the magnitude of the induced current is proportional to the change in the magnetic field. Therefore, by dynamically changing the magnetic field 360, a charge can be induced in the recipient's tissue in a manner that causes action potentials in the nerve cells (i.e., cause nerve cell firing). The magnetic field 360 can be dynamically changed by varying the current flow through stimulation coil 228.

In general, the induced current within the tissue flows substantially orthogonal to (i.e., at a right angle to) the magnetic field 360. As such, in the example of FIG. 3A, the induced tissue current will generally flow in circles in the same direction as the coil current. Nerve cells are not largely affected be the direction of the current, but rather by the magnitude of the current.

Figure 3C:
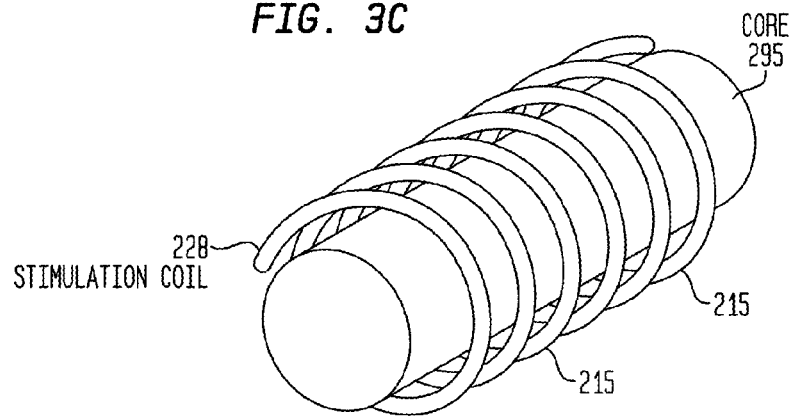
FIG. 3C is a perspective view of the stimulation coil of FIG. 3A shown with a core.

For ease of illustration, stimulation coils in accordance with embodiments presented herein are primarily shown and described without any type of magnetic core. However, it is to be appreciated that stimulation coils in accordance with embodiments presented herein may include magnetic cores or other types of cores. In general, a magnetic core is a piece of magnetic material with a high permeability used to confine and guide magnetic fields of the coil. Magnetic cores may be made from, for example, a ferromagnetic metal such as iron, or a ferrimagnetic compound such as ferrite. The presence of the magnetic core can increase the magnetic field of a coil over what it would be without the core. FIG. 3C illustrates an example in which stimulation coil 228 includes a magnetic core 295.

FIGS. 4A-4D are schematic diagrams illustrating the inducement of current at tissue through the use of an implanted stimulation coil (i.e., magnetic stimulation). For ease of illustration, FIGS. 4A-4D are described with reference to coil 228 of FIGS. 3A and 3B.

FIG. 4A illustrates the voltage (voltage signal) 462 that is applied to stimulation coil 228, while FIG. 4B illustrates the current 458 that flows through the coil in response to the applied voltage 462 of FIG. 4A. FIG. 4C illustrates the magnetic field 460 induced at target neurons (i.e., within tissue proximate to stimulation coil 228), while FIG. 4D illustrates the voltage 464 induced at the target neurons. FIG. 4E illustrates the current 466 induced at the target neurons.

Electrical stimulating prostheses typically use constant "current stimulation" to cause neural activation. That is, a constant current is delivered to an implanted electrical stimulating contact for subsequent delivery of the current to the recipient's tissue. The current is delivered in a manner that ensures that the net amount of charge delivered to the tissue is zero. In contrast, embodiments presented herein may use "voltage stimulation" to cause neural activation. That is, as shown in FIG. 4A, a voltage 462 is applied to the stimulation coil 228. The applied voltage 462 includes a plurality of voltage pulses 468. In the specific example of FIG. 4A, the voltage pulses 468 are biphasic voltage pulses 468 (i.e., voltage pulses having positive and negative components). It is to be appreciated that the use of biphasic voltage pulses 468 is illustrative and other coil excitation voltage signals (e.g., non-biphasic pulses) may be used in alternative embodiments.

As shown in FIG. 4B, the applied voltage 462 causes a ramped current through the coil. More specifically, each biphasic voltage pulse (with inter-phase gaps) 468 induces a substantially trapezoidal current pulse 470 in the stimulation coil 228. Each trapezoidal current pulse 470 has a positive slope/ramp 472, a top region (peak) 474, that a negative slope 476.

As shown in FIG. 4C, the coil current 458 generates a corresponding magnetic field 460 within the recipient's tissue. That is, the magnetic field 460 includes field changes 478 that correspond to the trapezoidal current pulses 470. As shown in FIGS. 4D and 4E, the field changes 478 induce approximate biphasic voltage pulses 480 and approximate biphasic current pulses 482 within the recipient's tissue. In other words, the end outcome of the applied voltage 462 is induced biphasic voltage and biphasic current within the recipient's tissue.

As noted above, FIG. 4A illustrates an example arrangement in which biphasic voltage pulses are applied to stimulation coil 228 to induce substantially trapezoidal current pulses (FIG. 4B). In accordance with alternative arrangements, current, rather than voltage, is be applied directly to the stimulation coil 228 to generate the substantially trapezoidal current pulses (i.e., current stimulation). In such examples, the substantially trapezoidal current pulses are created through, for example, the use of quantized current levels.

Figure 5:
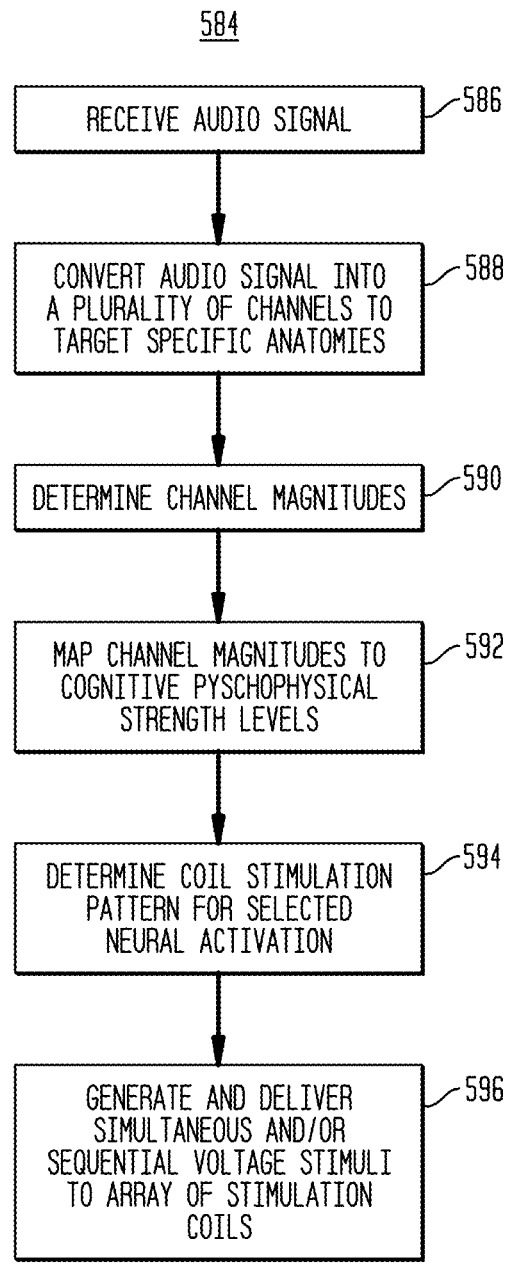
FIG. 5 is a flowchart of a method in accordance with embodiments presented herein.

Embodiments of the present invention are directed to tissue-stimulating auditory prostheses, such as cochlear implants, that utilize implantable stimulation coils to stimulate target populations of nerve cells of a recipient. A specific aspect of the use of stimulation coils in tissue-stimulating auditory prostheses is that the stimulation is indirect (i.e., induced by the magnetic field) and is configured to evoke perception by the recipient of a corresponding sound signal. That is, the stimulation coils should be driven in a manner that induces the activation of nerve cells in a manner that causes the recipient to perceive different target sounds. FIG. 5 is a flowchart illustrating an example method 584 for the real-time processing of an input audio signal by a cochlear implant for generation of magnetic stimulation. Merely for ease of illustration, method 584 is described with reference to cochlear implant 200 of FIG. 2.

Method 584 begins at 586 where an audio signal is received by the cochlear implant 200 and converted into one or more electrical signals (e.g., signals 246 in FIG. 2). The audio signal is, in general, a broadband and real-time signal that is to be perceived by the recipient. The audio signal is received, for example, by the microphone 208 or another sound input mechanism (e.g., an external microphone, an external audio port, etc.).

The effectiveness of cochlear implant stimulation depends, at least in part, on the place along the basilar membrane where the stimulation is delivered. That is, the cochlea of a recipient has characteristically been referred to as being "tonotopically mapped" in that regions of the cochlea toward the basal end are more responsive to high frequency signals, while regions of cochlea toward the apical end are more responsive to low frequency signals. These tonotopical properties of the cochlea are exploited in a cochlear implant by delivering stimulation within a predetermined frequency range to a region of the cochlea that is most sensitive (or would have been in a normal hearing person) to that particular frequency range. Therefore, at 588 of method 584, the electrical signals undergo pre-processing to, for example, convert the broadband audio signal into a plurality of frequency channel signals (i.e., signals that each correspond to a frequency or stimulation "channel" of the cochlear implant 200). As used herein, a frequency or stimulation channel refers to a signal processing chain that terminates in one or more coils arranged (e.g., orientated, located, etc.) to target specific auditory anatomies, such as different frequency regions of the cochlea nerve cells (i.e., cochlea basilar membrane). The channel signals are generated, for example, using a bank of band-pass filters, a Fast Fourier Transform (FFT), etc.

In certain embodiments, the stimulation channels are "real" channels having a one-to-one correspondence with the implanted stimulation coils (i.e., each channel terminates in an associated stimulation coil); while in other embodiments the stimulation channels are each associated with multiple stimulation coils. In these embodiments, the stimulation coil(s) are positioned proximate to a specific frequency region of the cochlea such that delivery of stimulation via those channels evokes perception of the associated frequency. However, certain constraints make it difficult to position one or more stimulation coils proximate to each and every frequency region of the cochlea. As such, certain embodiments presented herein make use of "virtual" stimulation channels that are created by combining stimulation from multiple stimulation coils positioned proximate to different frequency regions. For example, a virtual stimulation channel is utilized to stimulate a frequency region that is between the frequencies corresponding to two stimulation coils (i.e., between two real channels). As such, by appropriately stimulating two or more of the stimulation coils, the frequency corresponding to the virtual channel (i.e., the region between the two stimulation coils) is perceived by the recipient. The virtual stimulation channels are treated identically to real stimulation channels in accordance with the embodiments presented herein.

Returning to the specific example of FIG. 5, at 590 the sound processor 212 extracts envelope amplitude information, sometimes referred to herein as a channel magnitude, in each frequency band. These channel magnitudes, which represent the channel strength (from the input audio signal) and affect the gradient of the pulse slope or the maximum current level to be achieved over a specific time, are used to determine the level of stimulation current to be induced at each stimulation channel. More specifically, at 592, the channel magnitudes are mapped to psychophysical strength levels that, for the particular recipient, will best result in perception of the audio signal. This mapping, which is based on a number of different processing strategies and parameters, including various recipient specific parameters, results in the determination of a selected loudness for all or a subset of the stimulation channels. At 594, the channel loudness is used to determine a coil stimulation pattern that would cause a selected neural activation. That is, the channel loudness is used to determine a pattern of sequential and/or simultaneous activation of the stimulation coils to induce current in specific anatomical regions of the cochlea. At 596, based on data signals (e.g., signals 248 in FIG. 2) received from the sound processing unit 12, the coil drive unit 220 generates simultaneous and/or sequential voltage stimuli (voltage pulses) in accordance with the selected pattern and delivers the voltage stimuli to the array 226 of stimulation coils 228 in stimulating assembly 218 to evoke perception of the original input audio signal.

Figure 6:
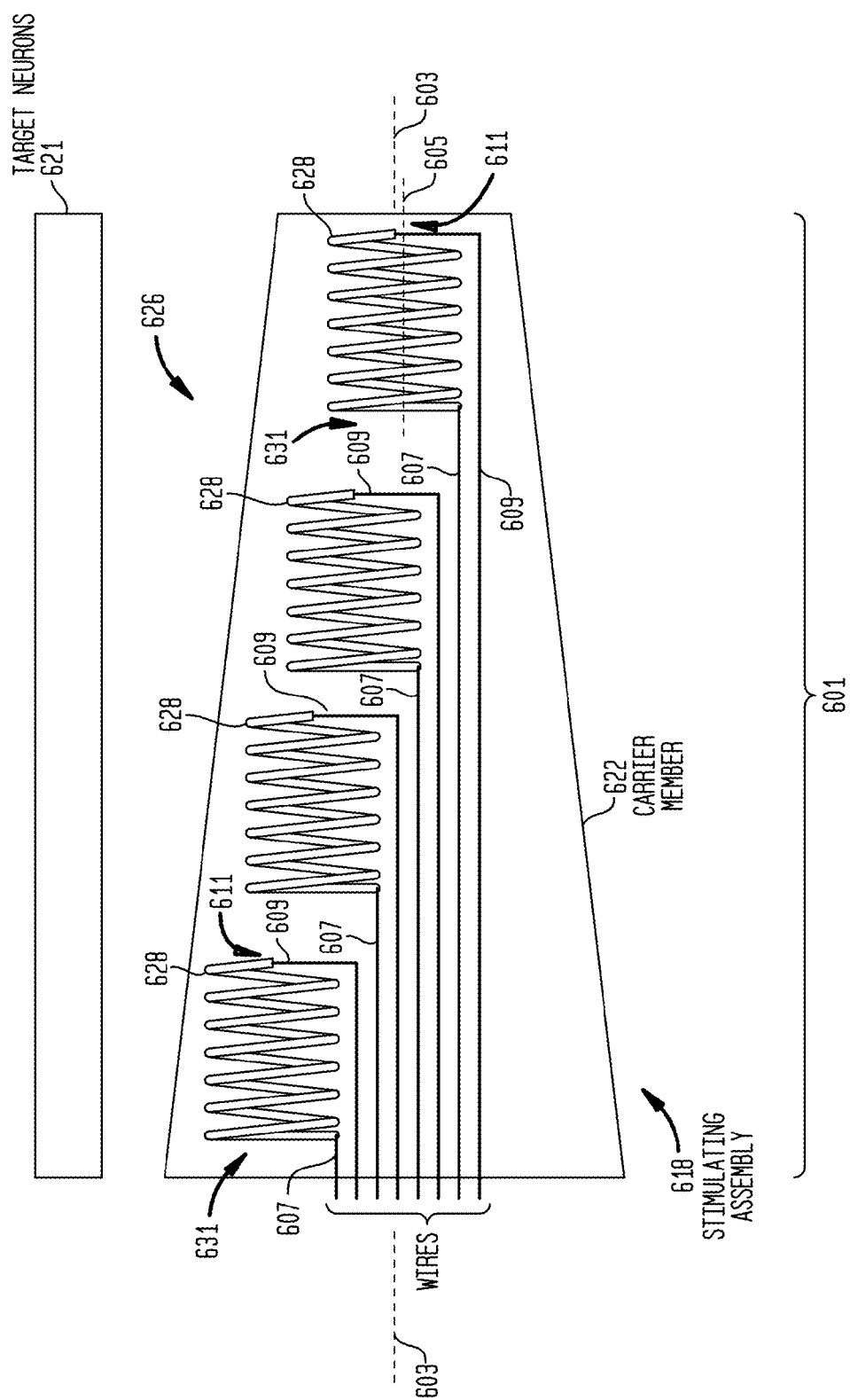
FIG. 6 is a cross-sectional side view of a section of a stimulating assembly that includes an array of stimulation coils in accordance with embodiments presented herein.

As noted above, embodiments presented herein utilize arrays of multiple stimulation coils to induce current in a recipient's tissue. The multiple stimulation coils in accordance with embodiments of the present invention may be configured in a number of different orientations or arrangements. For example, FIG. 6 is cross-sectional side view of a section 601 of an intra-cochlear stimulating assembly 618 having an array 626 of stimulation coils 628 disposed therein to stimulate target neurons 621.

Stimulating assembly 618 comprises a carrier member 622 formed from, for example, an elastomer material (e.g., silicone). Disposed in the carrier member 622 is a plurality of stimulation coils 628. FIG. 6 illustrates a specific section 601 of the stimulating assembly 618 that includes four (4) stimulation coils 628 that are fully/completely encapsulated within the carrier member 622 (i.e., no portions of the coils 618 are exposed to, or in contact with, the recipient's tissue, fluids, etc.). The full encapsulation of the stimulation coils 628 enables current to be induced in the recipient's tissue (target neurons 621) without galvanic contact, thereby eliminating problems associated with conventional electrical stimulating contacts and the contact/tissue interface.

As noted, intra-cochlear stimulating assemblies, such as stimulating assembly 618, are generally flexible so as to adopt a curved configuration when implanted into the cochlea. Intra-cochlear stimulating assemblies may be molded in a straight configuration or in a pre-curved configuration and straightened through the use of a stiffening element (e.g., sheath, stylet, etc.). As such, stimulating assembly 618 has a generally straight configuration prior to implantation that enables the surgeon to insert the stimulating assembly in the cochlea. When in the generally straight (pre-implantation) configuration, the stimulating assembly 618 is referred to as having an elongate central axis 603 extending longitudinally through the geometric center of the stimulating assembly. Also when in the generally straight configuration, the stimulation coils 628 are each referred to as having an elongate central axis 605 extending longitudinally through the geometric center of the respective coil. As shown, prior to implantation, the stimulation coils 628 are oriented such that the axes 605 of the coils are substantially parallel to the axis 603 of the stimulating assembly. In other words, the stimulation coils 628 are generally oriented along (i.e., substantially parallel to) the elongate length of the stimulating assembly 618.

When stimulating assembly 618 is implanted into a recipient's cochlea, the stimulating assembly will take a curved configuration corresponding to the spiral shape of the cochlea. Due to the orientation of the stimulation coils 628 along the elongate length of the stimulating assembly 618, the stimulation coils 628 are, when implanted, each oriented generally parallel to the associated target neurons (i.e., the elongate central axis 605 of each coil is generally parallel to the neurons that are to be stimulated by the coil). That is, the stimulation coils 628 are, when implanted, each oriented generally parallel to the surface of the corresponding canal (typically the Scala Tympani) covering the target neurons 621 (i.e., the elongate central axis 605 of the coils roughly approximates the spiral axis of the cochlea).

FIG. 6 also illustrates that each of the stimulation coils 628 are connected to two (2) wires, namely a source/drive wire 607 and a return wire 609. The drive wires 607 connect a first end 631 of each of the stimulation coils 628 to a coil drive unit (not shown in FIG. 6) for the delivery of current, while the return wires 609 connect a second end 611 of each of the stimulation coils 628 to the coil drive unit for the return of current. Voltage (or current) stimuli are applied to the stimulation coils 628 via the drive wires 607 and the induced or applied current passes through return wires 609 to back to the return(s) of the coil drive unit.

Similar to the embodiment of FIG. 2, the use of "source" or "drive" and "ground" or "return" to refer to the wires 607 and 609, respectively, is merely for ease of reference and does not limit the function of the wires. For example, in certain examples, voltage and/or current is applied to the stimulation coils 628 from either of the ends 631 or 611 to reverse the flow of current within a coil. As such, certain embodiments enable the use of the return wires 609 to apply signals to the stimulation coils 628 and the use of the drive wires 607 for the return of current.

As noted, FIG. 6 illustrates an example in which the stimulation coils 628 are generally oriented along the length of the stimulating assembly 618 such that, when implanted, the coils are generally parallel to different target populations of cochlea nerve cells. It is to be appreciated that other orientations for stimulation coils are possible in accordance with embodiments of the present invention. For example, FIG. 7 illustrates an alternative arrangement in which the stimulation coils are oriented generally orthogonal to the length of a stimulating assembly.

Figure 7:
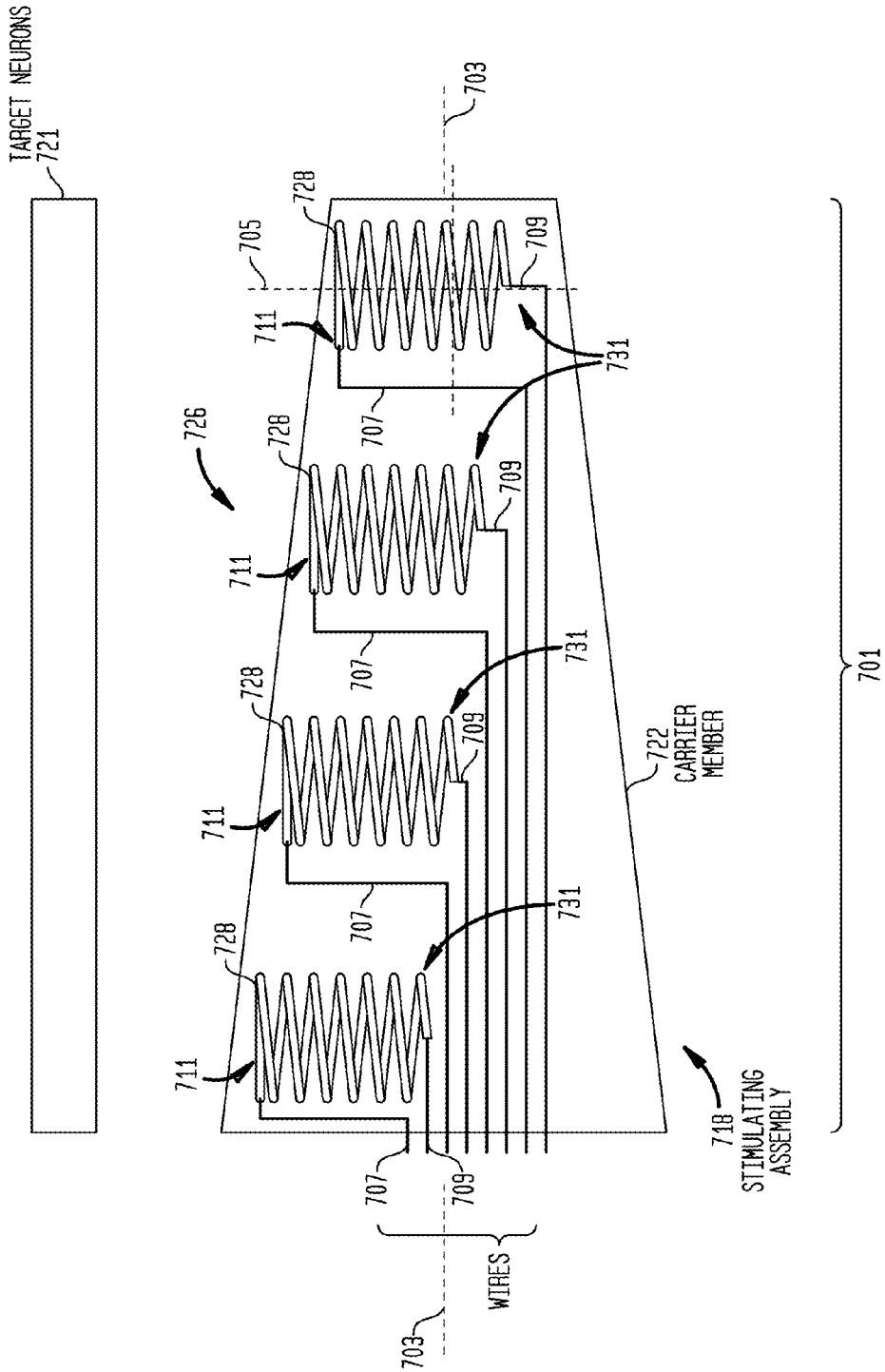
FIG. 7 is a cross-sectional side view of a section of another stimulating assembly that includes an array of stimulation coils in accordance with embodiments presented herein.

More specifically, FIG. 7 is cross-sectional side view of a section 701 of an intra-cochlear stimulating assembly 718 having an array 726 of stimulation coils 728 disposed in a carrier member 722 to stimulate target neurons 721. FIG. 7 illustrates a specific section 701 of the stimulating assembly 718 that includes four (4) stimulation coils 728 that are fully/completely encapsulated within the carrier member 722 (i.e., no portions of the coils 718 are exposed to, or in contact with, the recipient's tissue, fluids, etc.). The full encapsulation of the stimulation coils 728 enables current to be induced in the recipient's tissue without galvanic contact, thereby eliminating problems associated with conventional electrical stimulating contacts and the contact/tissue interface.

As noted above, intra-cochlear stimulating assemblies may be molded in a straight or pre-curved configuration and straightened through the use of a stiffening element. As such, stimulating assembly 718 has a generally straight configuration prior to implantation that enables the surgeon to insert the stimulating assembly in the cochlea. When in the generally straight (pre-implantation) configuration, the stimulating assembly 718 is referred to as having an elongate central axis 703 extending longitudinally through the geometric center of the stimulating assembly. Also when in the generally straight configuration, the stimulation coils 728 are each referred to as having an elongate central axis 705 extending longitudinally through the geometric center of the respective coil. As shown, prior to implantation, the stimulation coils 728 are oriented such that the axes 705 of the coils are substantially orthogonal (i.e., perpendicular) to the axis 703 of the stimulating assembly. In other words, the stimulation coils 728 are generally oriented orthogonal (i.e., substantially perpendicular to) the elongate length of the stimulating assembly 718 such that the coil axes 705 lie perpendicular to the stimulating assembly axis 703.

When stimulating assembly 718 is implanted into a recipient's cochlea, the stimulating assembly will take a curved configuration corresponding to the spiral shape of the cochlea. Due to the orientation of the stimulation coils 728 orthogonal to the elongate length of the stimulating assembly 718, the stimulation coils 728 are, when implanted, each oriented generally orthogonal to the associated target neurons (i.e., the elongate central axis 705 of each coil is generally perpendicular to the neurons that are to be stimulated by the coil). In this configuration, the second end 711 of each stimulation coil 728 is the part of the respective coil that is closest to the target neurons. That is, the stimulation coils 728 are, when implanted, each oriented generally perpendicular to the surface of the corresponding canal (typically the Scala Tympani) covering the target neurons 721.

FIG. 7 also illustrates that each of the stimulation coils 728 are connected to two (2) wires, namely a drive wire 707 and a return wire 709. The drive wires 707 connect a first end 731 of each of the stimulation coils 728 to a coil drive unit (not shown in FIG. 7) for the supply of current, while the return wires 709 connect the second end 711 of each of the stimulation coils 728 to the coil drive unit for the return of current. Voltage (or current) stimuli are applied to the stimulation coils 728 via the drive wires 707 and the induced or applied current passes through return wires 709 to the coil drive unit. Similar to the embodiment of FIG. 6, voltage and/or current is, in certain embodiments, applied to the stimulation coils 728 from either of the ends 731 or 711 to reverse the flow of current within a coil.

As noted, FIG. 7 illustrates an example in which the stimulation coils 728 are generally oriented orthogonal of the stimulating assembly 718 such that, when implanted, the coils are generally perpendicular to the target neurons. It is to be appreciated that other orientations for stimulation coils are possible in accordance with embodiments of the present invention. For example, FIG. 8 illustrates an alternative arrangement in which the stimulation coils are also oriented generally orthogonal to the length of a stimulating assembly.

More specifically, FIG. 8 is a cross-sectional side view of a section 801 of an intra-cochlear stimulating assembly 818 having an array 826 of stimulation coils 828 disposed in a carrier member 822 to stimulate target neurons 821. FIG. 8 illustrates a specific section 801 of the stimulating assembly 818 that includes four (4) stimulation coils 828 that are fully/completely encapsulated within the carrier member 822 (i.e., no portions of the coils 818 are exposed to, or in contact with, the recipient's tissue, fluids, etc.). The full encapsulation of the stimulation coils 828 enables current to be induced in the recipient's tissue without galvanic contact, thereby eliminating problems associated with conventional electrical stimulating contacts and the contact/tissue interface.

As noted above, intra-cochlear stimulating assemblies may be molded in a straight or pre-curved configuration and straightened through the use of a stiffening element. As such, stimulating assembly 818 has a generally straight configuration prior to implantation that enables the surgeon to insert the stimulating assembly in the cochlea. When in the generally straight (pre-implantation) configuration, the stimulating assembly 818 is referred to as having an elongate central axis 803 extending longitudinally through the geometric center of the stimulating assembly. Also when in the generally straight configuration, the stimulation coils 828 are each referred to as having an elongate central axis 805 extending longitudinally through the geometric center of the respective coil. As shown, prior to implantation, the stimulation coils 828 are oriented such that the axes 805 of the coils are substantially transverse (i.e., perpendicular) to the axis 803 of the stimulating assembly. In other words, the stimulation coils 828 are generally oriented orthogonal (i.e., substantially perpendicular to) the elongate length of the stimulating assembly 818 such that the coil axes 805 are substantially parallel to axis 803.

When stimulating assembly 818 is implanted into a recipient's cochlea, the stimulating assembly will take a curved configuration corresponding to the spiral shape of the cochlea. Due to the orientation of the stimulation coils 828 transverse to the elongate length of the stimulating assembly 818, the stimulation coils 828 are, when implanted, each oriented generally transverse to the associated target neurons (i.e., the elongate central axis 805 of each coil is generally transverse to the neurons that are to be stimulated by the coil). That is, the stimulation coils 828 are, when implanted, each oriented generally perpendicular to the surface of the corresponding canal (typically the Scala Tympani) covering the target neurons 821.

FIG. 8 also illustrates that each of the stimulation coils 828 are connected to two (2) wires, namely a drive wire 807 and a return wire 809. The drive wires 807 connect a first end (now shown in FIG. 8) of each of the stimulation coils 828 to a coil drive unit (also not shown in FIG. 8), while the return wires 809 connect a second end (also not shown in FIG. 8) of each of the stimulation coils 828 to the coil drive unit for the return of current. Voltage (or current) stimuli are applied to the stimulation coils 828 via the drive wires 807 and the induced or applied current passes through return wires 809 to the coil drive unit.

As noted, FIGS. 6-8 illustrate example orientations for stimulation coils. It is to be appreciated that other orientations for stimulation coils are possible. Also, although FIGS. 6-8 illustrate stimulation coils having an illustrative general cylindrical shape, it is to be appreciated that stimulation coils in accordance with embodiments presented herein may have a number of other shapes.

Figure 9A:
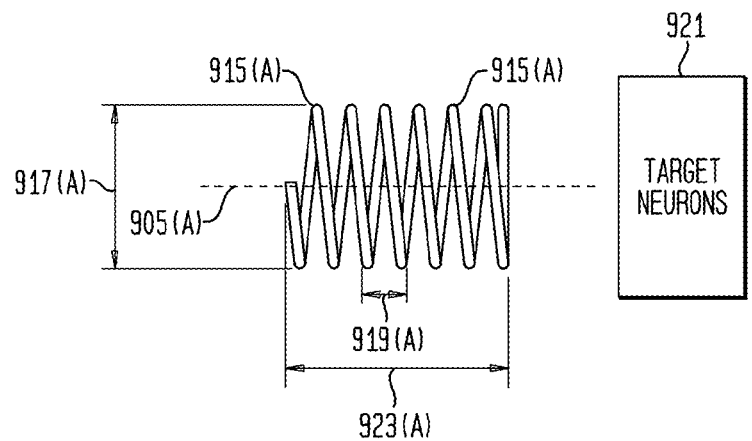
FIGS. 9A-9E are side views of stimulation coils in accordance with embodiments presented herein.

For example, FIGS. 9A-9E are diagrams illustrating side views of stimulation coils having different shapes in accordance with embodiments present herein. Referring first to FIG. 9A, a stimulation coil 928(A) is shown having a general cylindrical shape, similar to the coils shown in FIGS. 6-8. stimulation coil 928(A) is formed by a plurality of loops 915(A) of wire where all of the wire loops 915(A) have substantially the same diameter 917(A). That is, each of the loops 915(A) has substantially the same size and shape. Additionally, the loops 915(A) are separated by a substantially constant distance 919(A). In general, the "distance" between two loops 915(A) is measured between corresponding points in two consecutive loops. A central axis 905(A) of the stimulation coil 928(A) extends through the center of each of the loops 915(A). As shown, the stimulation coil 928(A) has a length 923(A) and is oriented so as to be substantially orthogonal to target neurons 921.

Figure 9B:
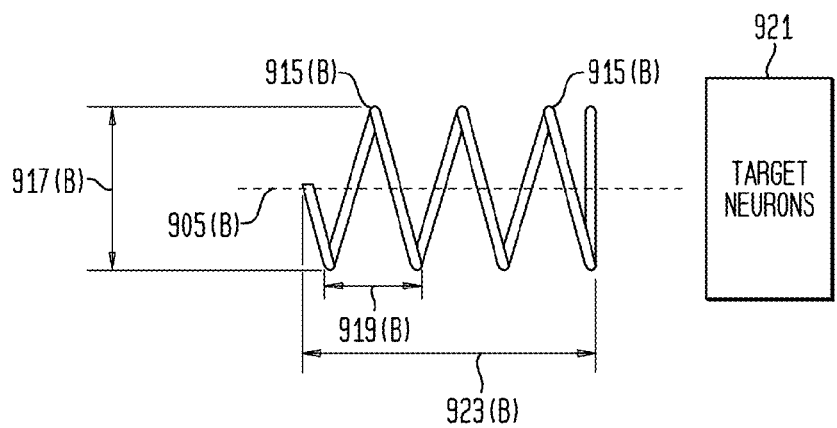

FIG. 9B illustrates another stimulation coil 928(B) having a general cylindrical shape that is similar to the stimulation coil 928(A) of FIG. 9A. That is, stimulation coil 928(B) is formed by a plurality of loops 915(B) of wire where all of the wire loops 915(B) have substantially the same diameter 917(B) (i.e., size and shape). A central axis 905(B) of the stimulation coil 928(B) extends through the center of each of the loops 915(B).

In the embodiment of FIG. 9B, the loops 915(B) are separated by a substantially constant distance 919(B) that is substantially larger than the distance 919(A) for the loops 915(A) of FIG. 9A. Due to the larger distance 919(B) separating the loops 915(B), the stimulation coil 928(B), when having substantially the same length 928(B) as coil 928(A) (FIG. 9A), the stimulation coil 928(B) includes fewer loops than coil 928(A) of FIG. 9A. In other words, the "loop density" of the stimulation coil 928(B) is lower than the loop density of stimulation coil 928(A).

Figure 9C:
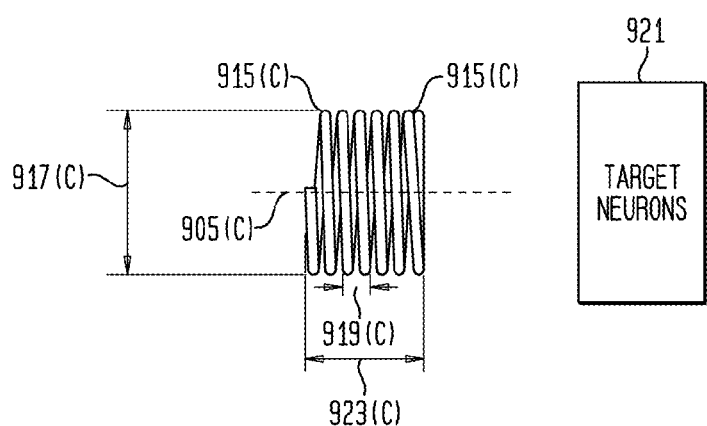

FIG. 9C illustrates another stimulation coil 928(C) having a general cylindrical shape that is similar to the stimulation coils 928(A) and 928(B) of FIGS. 9A and 9B, respectively. That is, stimulation coil 928(C) is formed by a plurality of loops 915(C) of wire where all of the wire loops 915(C) have substantially the same diameter 917(C) (i.e., size and shape). A central axis 905(C) of the stimulation coil 928(C) extends through the center of each of the loops 915(C).

In the embodiment of FIG. 9C, the loops 915(B) are separated by a substantially constant distance 919(C) that is substantially smaller than the distance 919(A) for the loops 915(A) of FIG. 9A. Due to the smaller distance 919(C) separating the loops 915(C), the stimulation coil 928(C) includes the same number of loops as coil 928(A) (FIG. 9A), but will have a substantially smaller overall length 923(C). In other words, the "loop density" of the stimulation coil 928(C) is greater than the loop density of both stimulation coils 928(A) (FIG. 9A) and 928(B) (FIG. 9B).

Figure 9D:
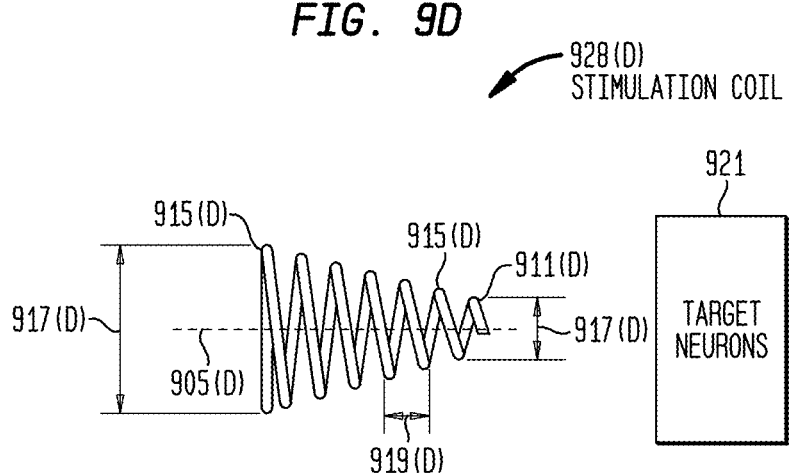

FIG. 9D illustrates a stimulation coil 928(D) having a general conical/tapered shape. stimulation coil 928(D) is formed by a plurality of loops 915(D) of wire where the wire loops 915(D) have a decreasing diameter 917(D) in the direction of the target neurons 921. That is, the size of each consecutive loop 915(D) decreases towards an end 911(D) that is configured to be positioned proximate to the target neurons 921. The loops 915(D) are separated by a substantially constant distance 919(D) and a central axis 905(D) of the stimulation coil 928(D) extends through the center of each of the loops 915(D). As shown, the stimulation coil 928(D) is oriented so as to be substantially orthogonal to target neurons 921.

Figure 9E:
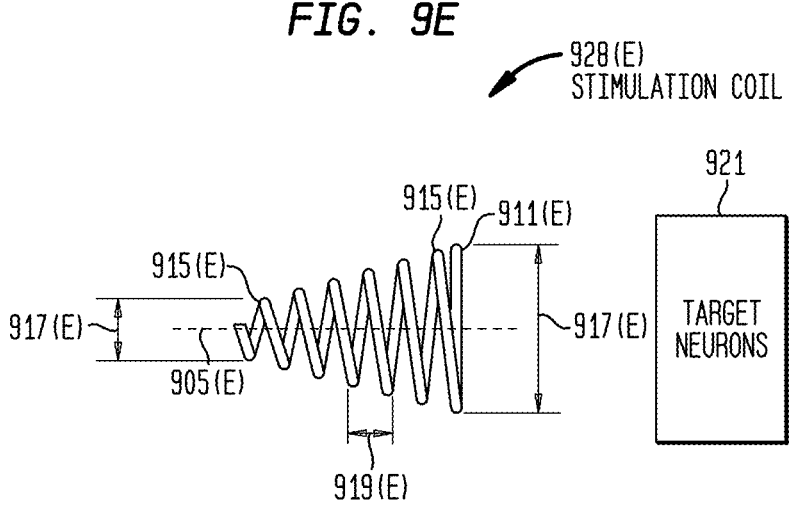

FIG. 9E illustrates a stimulation coil 928(E) having a general conical/tapered shape. stimulation coil 928(E) is formed by a plurality of loops 915(E) of wire where the wire loops 915(E) have an increasing diameter 917(E) in the direction of the target neurons 921. That is, the size of each consecutive loop 915(E) increases towards an end 911(E) that is configured to be positioned proximate to the target neurons 921. The loops 915(E) are separated by a substantially constant distance 919(E) and a central axis 905(E) of the stimulation coil 928(E) extends through the center of each of the loops 915(E). As shown, the stimulation coil 928(E) is oriented so as to be substantially orthogonal to target neurons 921.

The shapes for stimulation coils shown in FIGS. 9A-9E are illustrative. As such, it is to be appreciated that stimulation coils in accordance with embodiments of the present invention have shapes, orientations, and/or locations selected, for example, to facilitate implantation into the cochlea, to achieve a selected stiffness and/or flexibility for a stimulating assembly, to achieve selected frequency spacing, etc. Embodiments of the present invention may, for example, use short coils with tightly spaced loops, long coils with largely spaced loops, tapered coils, etc. to induce a magnetic field at the target neurons.

It is to be appreciated that the embodiments described herein are not mutually exclusive and may be combined with one another in various arrangements. For example, it is to be appreciated that the stimulation coils shown in FIGS. 9A-9E may be used in different orientations or arrangements shown in FIGS. 6-8 or in other configurations/arrangements.

In accordance with certain embodiments presented herein, multiple coils may be utilized concurrently/together (i.e., simultaneously and/or sequentially) to activate a recipient's tissue. For example, FIG. 10 illustrates an arrangement in which two stimulation coils 1028(A) and 1028(B) are activated together to stimulate target neurons 1021.

Figure 10:
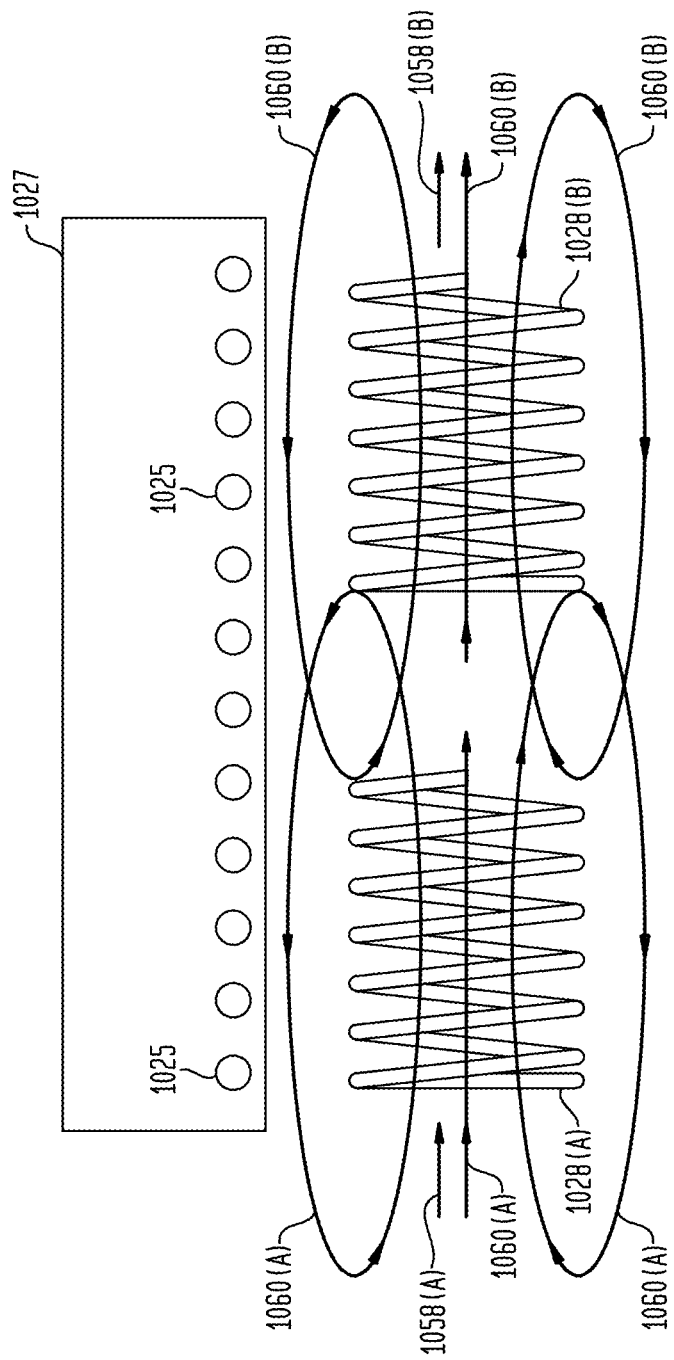
FIG. 10 is a diagram illustrating the delivery of synchronous stimulation by multiple stimulation coils in accordance with embodiments presented herein.

In the arrangement of FIG. 10, voltage signals are applied to each of the stimulation coils 1028(A) and 1028(B) to induce coil currents, the general direction of which are shown by arrows 1058(A) and 1058(B), respectively. These coil currents 1058(A) and 1058(B) cause the stimulation coils 1028(A) and 1028(B) to generate magnetic fields 1060(A) and 1060(B), respectively, that pass through a recipient's tissue 1027. The induced coil currents 1058(A) and 1058(B) are such that the magnetic fields 1060(A) and 1060(B) have substantially the same directions. As such, the magnetic fields 1060(A) and 1060(B) collectively activate an area of the recipient's tissue 1027 that is substantially wider than an area that is activated by a single stimulation coil. In FIG. 10, the circles 1025 illustrate areas of the target neurons that may be activated by the magnetic fields 1060 (A) and 1060(B).

The arrangement of FIG. 10 is useful, for example, to reduce the power consumption of a cochlear implant. More specifically, the wider activation area caused by utilizing both of the stimulation coils 1028(A) and 1028(B) together results in activation of the target neurons with, for example, lower magnetic field strengths requiring less induced current, lower applied voltage, and thus lower power requirements.

Figure 11:
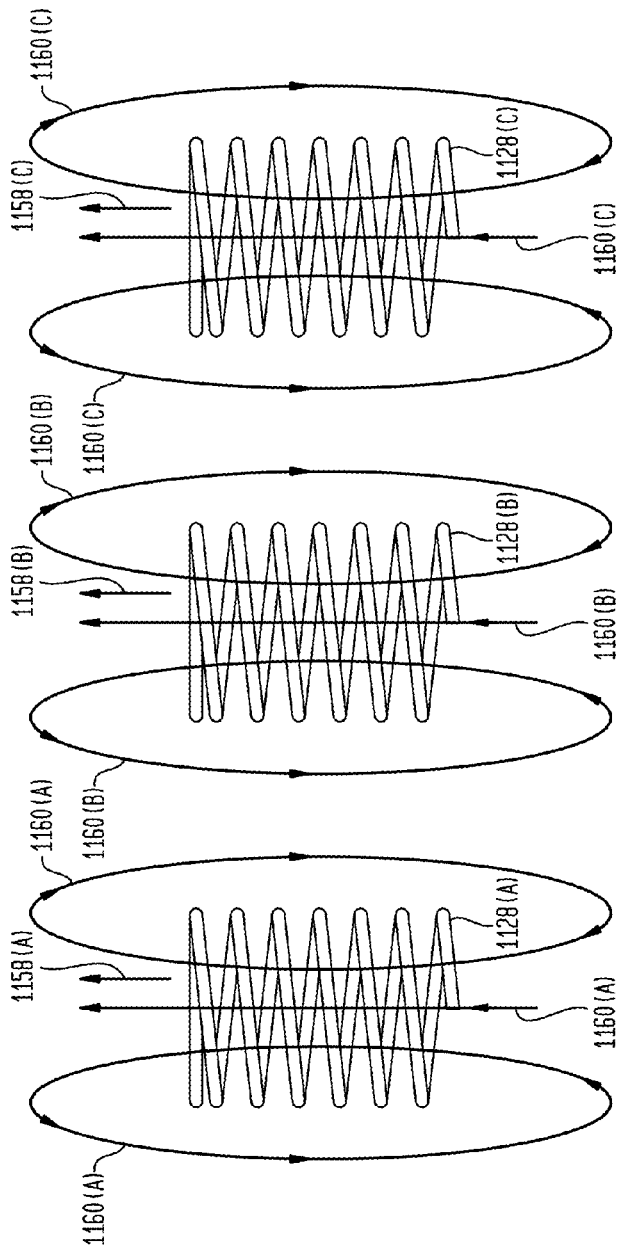
FIG. 11 is another diagram illustrating the delivery of synchronous stimulation by multiple stimulation coils in accordance with embodiments presented herein.

FIG. 11 illustrates an arrangement in which three (3) stimulation coils 1128(A), 1128(B), and 1128(C) are activated together to stimulate target neurons within a recipient's tissue 1127. In the arrangement of FIG. 11, voltage signals are applied to each of the stimulation coils 1128(A), 1128(B), and 1128(C) to induce coil currents, the general direction of which are shown by arrows 1158(A), 1158(B), and 1158(C), respectively. These coil currents 1158(A), 1158(B), and 1158(C) cause the stimulation coils 1128(A), 1128(B), and 1128(C) to generate magnetic fields 1160(A), 1160(B), and 1160(C), respectively, that pass through the recipient's tissue 1127. The induced coil currents 1158(A), 1158(B), and 1158(C) are such that the magnetic fields 1160(A), 1160(B), and 1160(C) have substantially the same directions.

In the specific arrangement of FIG. 11, the stimulation coils 1128(A), 1128(B), and 1128(C) are positioned parallel to one another, but generally orthogonal to the recipient's tissue. In this arrangement, magnetic field 1160(B) will overlap with both magnetic fields 1060(A) and 1060(C) in different areas of the recipient's tissue. In the regions where magnetic field 1160(B) overlaps with each of the magnetic fields 1060(A) and 1060(C), the direction of the two magnetic fields will cause cancellation of induced currents. More specifically, currents in the tissue are induced in a circular fashion that matches the flow of the current in the coil. That is, at the locations of the neurons, the current is in a circle (e.g., general donut shape) travelling in the same direction as the current was traveling in the coil. Therefore, in the arrangement of FIG. 11, the magnetic fields at the location of the neurons will induce "circles" of current which, in the spaces between stimulating coils, will overlap and cancel since the induced "circles" of current will be in opposite directions at the overlapping areas.

In FIG. 11, the circles 1125 illustrate areas of target neurons that are activated by the magnetic fields 1160(A)-1060(C), while the dashes 1129 illustrate areas of the recipient's tissue in which the induced currents are cancelled as a result of the overlapping magnetic fields. The cancelling of induced currents as shown in FIG. 11 is used to narrow activation areas.

Figure 12:
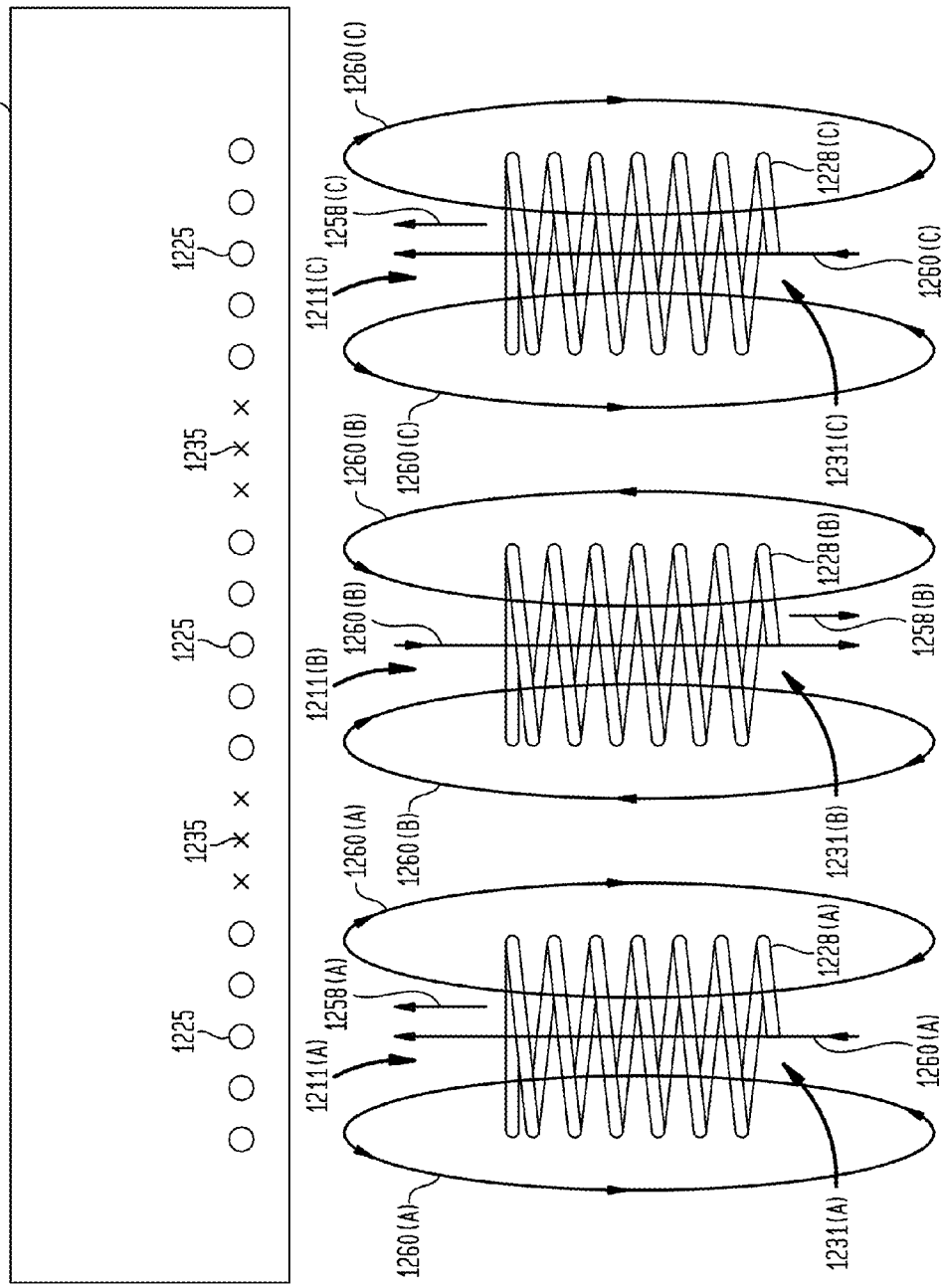
FIG. 12 is another diagram illustrating the delivery of synchronous stimulation by multiple stimulation coils in accordance with embodiments presented herein.

FIG. 12 illustrates another arrangement in which three (3) stimulation coils 1228(A), 1228(B), and 1228(C) are activated together to stimulate target neurons within a recipient's tissue 1227. In the arrangement of FIG. 12, voltage signals are applied to each of the stimulation coils 1228(A), 1228(B), and 1228(C) to induce coil currents, the general direction of which are shown by arrows 1258(A), 1258(B), and 1258(C), respectively. These coil currents 1258(A), 1258(B), and 1258(C) cause the stimulation coils 1228(A), 1228(B), and 1228(C) to generate magnetic fields 1260(A), 1260(B), and 1260(C), respectively, that pass through the recipient's tissue 1127. The induced coil currents 1258(A) and 1258(C) are such that the magnetic fields 1260(A) and 1260(C) have substantially the same directions. That is, coil currents 1258(A) and 1258(C) flow from a first end 1231(A) and 1231(C), respectively, to a second end 1211(A) and 1211(C), respectively, of the coils 1228(A) and 1228(C). However, coil current 1258(B) passes through coil 1228(B) in a direction that is substantially opposite to coil currents 1258(A) and 1258(C) (i.e., coil current 1258(B) passes from second end 1211(B) to 1231(B)). As such, the magnetic filed 1260(B) induced by coil current 1258(B) flows in a direction that is opposite to magnetic fields 1260(A) and 1260(C).

In the specific arrangement of FIG. 12, the stimulation coils 1228(A), 1228(B), and 1228(C) are positioned parallel to one another, but generally orthogonal to the recipient's tissue. In this arrangement, magnetic field 1260(B) will overlap with both magnetic fields 1260(A) and 1260(C) in different areas of the recipient's tissue. In the regions where magnetic field 1260(B) overlaps, in between two coils, with each of the magnetic fields 1260(A) and 1260(C), the direction of the two overlapping magnetic fields will cause summation of induced currents. In FIG. 12, the circles 1225 illustrate areas of the recipient's tissue that are activated by the magnetic fields 1260(A)-1260(C), while the "Xs" 1235 illustrate areas of the recipient's tissue in which the induced currents are summed as a result of the overlapping magnetic fields. The summation of induced currents as shown in FIG. 12 is used to, for example, narrow activation areas, steer activation, or to reduce power requirements.

Certain embodiments described above illustrate stimulation coils where the opposing ends of the coils are connected to different wires. In some such embodiments, the two wires are referred to as a source/drive wire and a ground/return wire, respectively. As noted above, the use of "source" or "drive" and "ground" or "return" are provided for ease of reference and do not limit the function of the wires. For example, in certain examples, voltage and/or current may be applied to stimulation coils from either of the coil ends to reverse the flow of current within a coil. As such, certain embodiments enable the use of the return wires to apply signals to the stimulation coils and the use of the drive wires for the return of current. In such examples, switching circuitry is provided in the coil drive unit or other component to enable current to flow through the stimulation coils in different directions.

Figure 13:
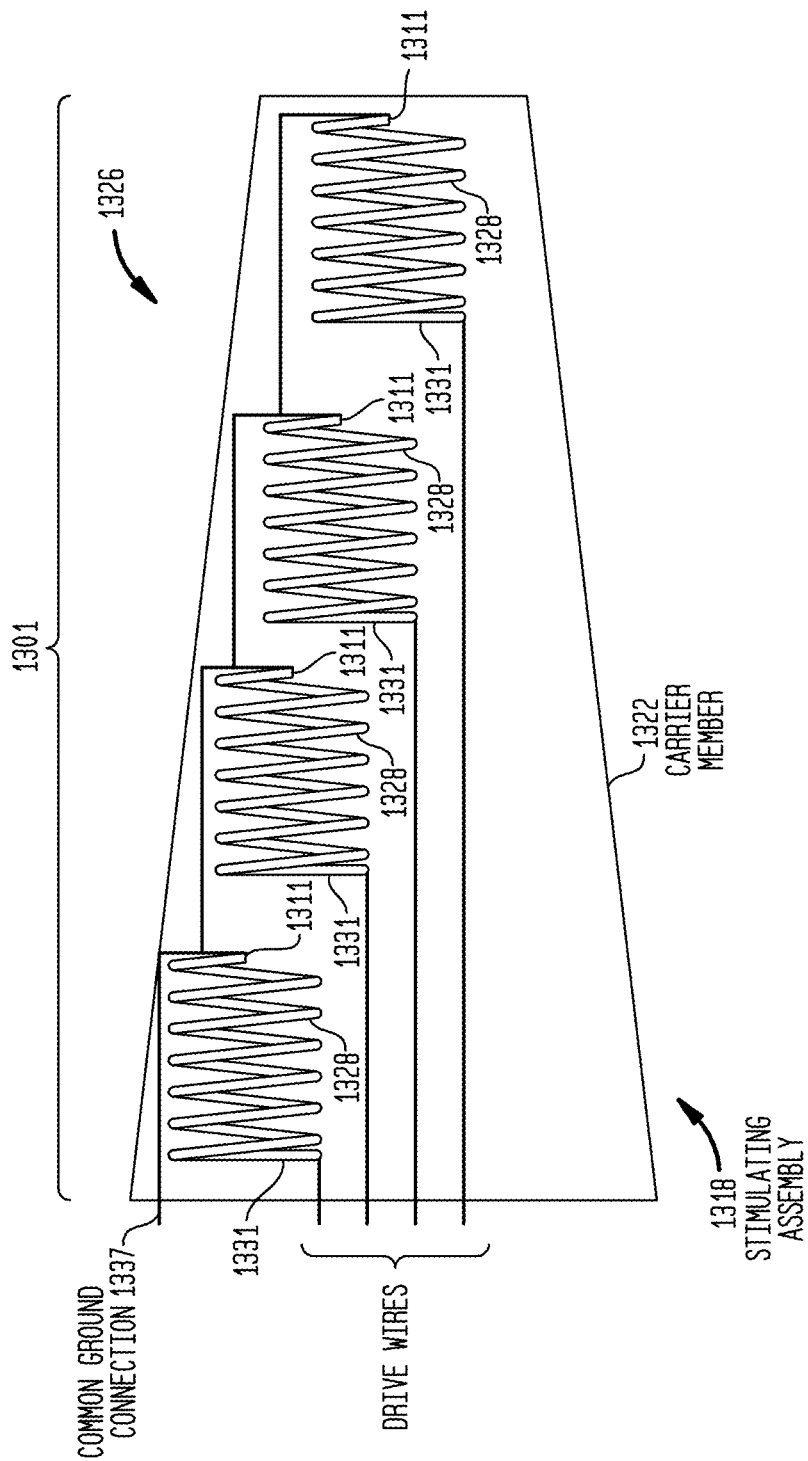
FIG. 13 is a cross-sectional side view of a section of another stimulating assembly that includes an array of stimulation coils in accordance with embodiments presented herein.

FIG. 13 illustrates a specific arrangement in which multiple stimulation coils are connected to a single ground. More specifically, FIG. 13 is a cross-sectional side view of a section 1301 of an intra-cochlear stimulating assembly 1318 having an array 1326 of stimulation coils 1328 disposed therein.

Stimulating assembly 1318 comprises a carrier member 1322 formed, for example, from an elastomer material. Disposed in the carrier member 1322 is a plurality of stimulation coils 1328. FIG. 13 illustrates a specific section 1301 of the stimulating assembly 1318 that includes four (4) stimulation coils 1328 that are fully/completely encapsulated within the carrier member 1322.

FIG. 13 illustrates that each of the stimulation coils 1328 are connected to two (2) wires, namely individual source/drive wires 1307 and a common ground wire 1339. The individual drive wires 1307 separately connect a first end 1331 of each of the stimulation coils 1328 to a coil drive unit (not shown in FIG. 13), while the common ground wire 1339 connects all of the second ends 1311 of the stimulation coils 1228 together and to a ground element (also not shown in FIG. 13). In other words, the ground wire 1339 connects together the second ends 1311 to form a common ground connection 1337. Voltage (or current) stimuli are applied to the stimulation coils 1328 via the drive wires 1307 and the induced or applied current passes to the common ground connection 1337 formed by the ground wire 1339.

Figure 14:
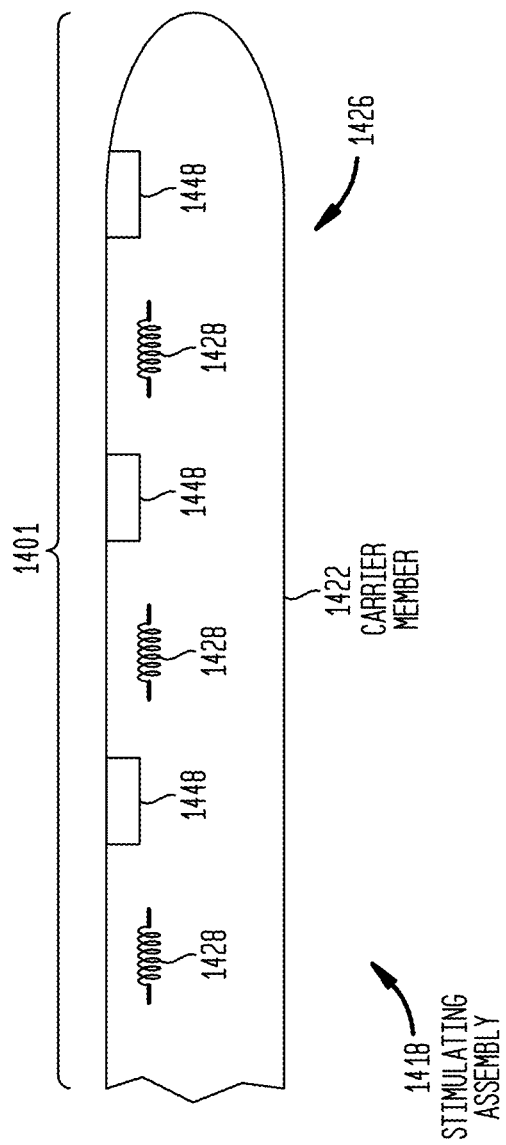
FIG. 14 is a cross-sectional side view of a section of another stimulating assembly that includes an array of stimulation coils in accordance with embodiments presented herein.

FIG. 14 illustrates an embodiment of the present invention in which magnetic stimulation is combined with one or more other stimulation techniques (e.g., electrical, optical, mechanical, etc.). More specifically, FIG. 14 is a cross-sectional side view of a section 1401 of an intra-cochlear stimulating assembly 1418 comprising a carrier member 1422. Disposed in the carrier member 1422 is a stimulating array 1426 formed from a plurality of stimulation coils 1428 and a plurality of stimulating contacts 1498. FIG. 14 illustrates a specific section 1401 of the stimulating assembly 1418 that includes three (3) stimulation coils 1428 that are fully/completely encapsulated within the carrier member 1422 and three (3) electrical stimulating contacts 1498 at the surface of the carrier member 1422. In accordance with embodiments presented herein, the stimulation coils 1428 and the electrical stimulating contacts 1498 may be utilized separately or together (i.e., simultaneously or sequentially) in various combinations to, for example, lower overall stimulus level needed to activate target neuron populations, stimulate different nerve cell populations, etc.

Although FIG. 14 illustrates the stimulation coils 1428 and the electrical stimulating contacts 1498 in an alternating arrangement, it is to be appreciated that this arrangement is merely illustrative. More specifically, the stimulation coils 1428 and the electrical stimulating contacts 1498 are positioned to activate regions of the cochlea that are most responsive to the respective type of stimulation. For example, a specific region of the cochlear is better activated by stimulation, such as the apex, due to anatomical differences, while other regions of the cochlea are more responsive to electrical stimulation.

Embodiments have been primarily described above with reference to stimulation coils implanted in a recipient's cochlea. It is to be appreciated that embodiments of the present may also make use of extra-cochlear stimulation coils in addition to, or instead of, the stimulation coils. As used herein, an extra-cochlear stimulation coil is an implantable magnetic coil having a size configuration such that it cannot be positioned immediately adjacent to target nerve cells. In the context of cochlear implants, a extra-cochlear stimulation coil has a size that it cannot be implanted within the recipient's cochlea, but can be implanted adjacent to the exterior of the cochlea (e.g., in the middle ear cavity).

Figure 15:
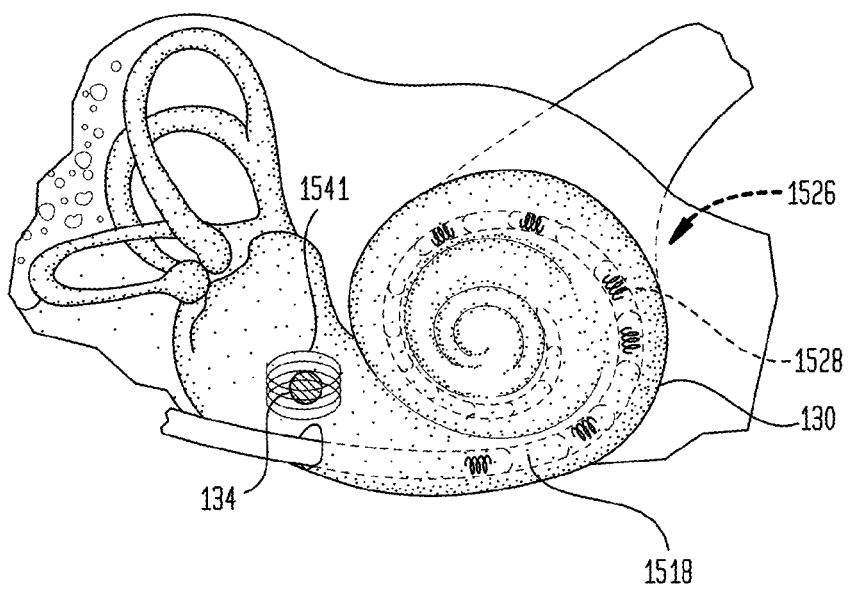
FIG. 15 is a schematic diagram of a extra-cochlear stimulation coil configured to deliver magnetic stimulation to a recipient in accordance with embodiments presented herein.

FIG. 15 illustrates an example embodiment that utilizes a extra-cochlear stimulation coil to "prime" a recipient's cochlea for magnetic stimulation, electrical stimulation, etc. More specifically, as shown in FIG. 15, a extra-cochlear stimulation coil 1541 is implanted in a recipient outside of the cochlea 130. A stimulating assembly 1518 that includes an array 1526 of stimulating elements, such as stimulation coils, electrical stimulating contacts, optical stimulating contacts, etc. is implanted into the cochlea 130. FIG. 15 illustrates an array 1526 that includes a plurality of stimulation coils 1528.

In the arrangement of FIG. 15, the extra-cochlear stimulation coil 1541 is used to induce current within the cochlea nerve cells to provide a baseline level of activation aimed to lower the neural threshold needed by, for example, electrical, magnetic, acoustic, and/or mechanical stimulation. That is, the extra-cochlear implantable coil 1541 induces current at the cochlea nerve cells such that the nerve cells are activated to a level that is slightly below their firing threshold. Another type of stimulation, such as magnetic stimulation with the stimulation coils 1528, is then be applied to activate specific target populations of the cochlea nerve cells. Because the cochlea nerve cells are already close to their firing threshold (due to the stimulation applied by the extra-cochlear implantable coil 1541), a lower level of induced current is used by the stimulation coils 1528 to cause firing of the target nerve cells. The use of a lower induced current requires a lower applied voltage (or current) to the stimulation coils 1528, and thus reduces the power requirements for the cochlear implant.

In general, the overall power usage of a cochlear implant using an extra-cochlear stimulation coil is less than the power usage of a cochlear implant that includes only intra-cochlear stimulation coils because the larger extra-cochlear stimulation coil is more efficient than each of the intra-cochlear stimulation coils. Therefore, by using a more efficient coil to bring the cochlea nerve cells are already close to their firing threshold, and using less current to induce firing, the entire system becomes more efficient and consumes less power.

The stimulation provided by the extra-cochlear stimulation coil 1541 could be continuous (e.g., using pulses or a sinusoidal stimulus at a constant amplitude) to prime the neurons. Alternatively, the stimulation provided by the extra-cochlear stimulation coil 1541 could be provided immediately before, after, or simultaneously with, the stimulation from individual stimulation coils 1528 or other stimulating elements.

FIG. 15 illustrates an exemplary location of the implantable extra-cochlear stimulation coil 1541 near a recipient's round window 134. It is to be appreciated that this location is merely illustrative and that the extra-cochlear implantable coil 1541 could be at any location in proximity to the cochlea 130. It is also to be appreciated that multiple extra-cochlear implantable coils may be provided in alternative embodiments. In such embodiments, the different extra-cochlear implantable coils could be used to, for example, activate different regions of the cochlea at different times.

Extra-cochlear stimulation coils in accordance with embodiments of the present invention may also be placed within the eye in a similar fashion to prime retinal neurons for use with stimulation. Alternatively, extra-cochlear stimulation coils could also be placed in proximity to the semi-circular canals to activate the vestibular system with information on recipient orientation.

Figure 16:
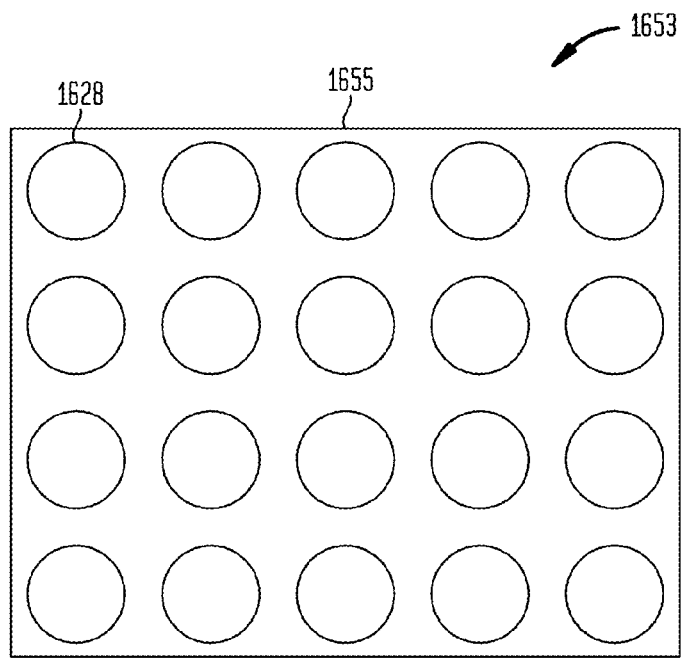
FIG. 16 is a diagram illustrating a planar arrangement of stimulation coils in accordance with embodiments presented herein.

Is also to be appreciated that embodiments of the present invention may use stimulation coils in different arrangements and locations other than within a recipient's cochlea. For example, stimulation coils could be used for activation of any region of the brain or nervous system to treat, Parkinson's disease, epilepsy, bipolar, schizophrenia, obsessive compulsive disorder, etc. FIG. 16 illustrates a planar arrangement 1653 of stimulation coils 1628 that are used, for example, to stimulate a surface, such as a retina. In this example, the stimulation coils 1628 are arranged on a substantially flat, and possibly flexible, substrate 1655, such as an ABI, Cortex, or Retinal surface electrode. Similar to the cochlear implant embodiments described above, the planar arrangement 1653 of FIG. 16 are configured for use in targeting a specific neural population with information from a real-time and real-world input.

The above embodiments have been primarily described with reference to wire stimulation coils for magnetic stimulation of a recipient. In accordance with certain embodiments, the stimulation coils are non-wire coils formed, for example, through lithography processes (e.g., using a silicone substrate in the nano-manufacturing of coils instead of wire coils). For example, FIG. 17 is a cross-sectional side view of a section 1701 of an intra-cochlear stimulating assembly 1718 comprising a carrier member 1722. Disposed in the carrier member 1722 is a stimulating array 1726 formed from a plurality of non-wire stimulation coils 1728. FIG. 17 illustrates a specific section 1701 of the stimulating assembly 1718 that includes three (3) non-wire stimulation coils 1728 that are fully/completely encapsulated within the carrier member 1722.

In arrangements using non-wire coils created through lithography, it is possible to include electronics local to the stimulation site (i.e., in proximity to the non-wire stimulation coils). For example, FIG. 17 illustrates a plurality local electronics packages 1797 that are each associated with one of the non-wire stimulation coils 1728. By locating electronics close to the non-wire stimulation coils 1728, the number of connecting wires may be reduced, thereby possibly leaving room for the addition of more stimulation coils when compared to arrangements that use wire coils and multiple connecting wires.

In certain embodiments, the electronics packages 1797 each include active components, such as a capacitor, data management components, and power management components. In certain examples, the non-wire stimulation coils 1728 may form part of the electronics packages 1797. Two or more wires could then be used, as each electronics packages 1797 could receive both power and data from as few as two wires to service all of the non-wire coils and electronics packages.

In embodiments in which the electronics packages 1797 include a capacitor (or other power storage element), the capacitor stores charge from the wires. The charge stored in the capacitor is maintained so as to ready to discharge through the connected stimulation coil 1728. Power management components are configured to receive the power from the wires and convert it into a form to change the capacitor. The received power could be constant direct current (DC), but in order to avoid using more than two wires the power may be an alternating signal that also encodes the data. DC could be avoided by switching the polarity of the two wires, e.g. at the data rate thus sending the power and the data by a single mechanism. Gradually transferring energy to a storage element is more efficient than rapid transfer to the coils.

The data management components received encoded data from the wires and decode the data to obtain the underlying information. The decoded information is used to inform one or more elements of the electronics packages 1797 of when and what sort of stimulus to produce (e.g., length, amplitude, timing). The system stimulator would be able to command each electronics packages 1797 and associated stimulation coil 1728 and to stimulate individually or as a group, through a coding and decoding method.

An advantage to the use of non-wire stimulation coils and local electronics is that (1) the power can be sent continuously at a lower current, which means a much lower power (or the same power usage, but much larger stimuli), and (2) there may only be two total wires that could be larger, thereby decreasing wire resistance further decreasing power consumption.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A cochlear implant, comprising:
   a substantially flexible stimulating assembly configured to be implanted into a recipient's cochlea adjacent to cochlea nerve cells;
   a plurality of stimulation coils positioned in the stimulating assembly; and
   a coil drive unit configured to apply drive signals to one or more of the plurality of stimulation coils to magnetically stimulate the cochlea nerve cells with the one or more stimulation coils.

2. The cochlear implant of claim 1, wherein the drive signals comprise voltage signals applied to the one or more stimulation coils to induce current within the one or more stimulation coils.

3. The cochlear implant of claim 1, wherein the drive signals comprise current signals applied to the one or more stimulation coils such that the current signals pass though the one or more stimulation coils.

4. The cochlear implant of claim 1, wherein each of the stimulation coils comprises:
   a first end that is connected to the coil drive unit via a drive wire such that the drive signals are applied at the first end; and
   a second end that is connected to the coil drive unit via a return wire such that signals return to the coil drive unit via the return wire.

5. The cochlear implant of claim 4, further comprising:
   a switching circuit connected to the drive wires and the return wires, wherein the switching circuit is configured to connect the second ends of the stimulation coils to the coil drive unit such that the drive signals are applied at the second end via the return wires and to connect the first ends of the stimulation coils to the coil drive unit such that signals return to the coil drive unit via the drive wires.

6. The cochlear implant of claim 1, further comprising:
   one or more sound input elements configured to receive a sound signal; and
   a sound processor configured to:
      extract, from the sound signal, a plurality of channel magnitudes representing the strength of the sound signal in different frequency channels, and
      utilize the channel magnitudes to determine the level of current to be induced at populations of cochlea nerve cells associated with each frequency channel.

7. The cochlear implant of claim 1, further comprising:
   one or more sound input elements configured to receive a sound signal; and
   a sound processor configured to:
      extract, from the sound signal, a plurality of channel magnitudes representing the strength of the sound signal in different frequency channels, and
      utilize the channel magnitudes to determine the level of voltage to be induced at populations of cochlea nerve cells associated with each frequency channel.

8. The cochlear implant of claim 1, wherein the coil drive unit is configured to concurrently apply drive signals to a plurality of stimulation coils to cause the plurality of stimulation coils to concurrently magnetically stimulate the cochlea nerve cells.

9. The cochlear implant of claim 1, further comprising:
at least one extra-cochlear stimulation coil configured to be implanted adjacent to the recipient's cochlea,
wherein the coil drive unit is configured to apply drive signals to the extra-cochlear stimulation coil to magnetically stimulate the cochlea nerve cells via the extra-cochlear stimulation coil.

10. The cochlear implant of claim 1, further comprising:
a plurality of electrical stimulating contacts disposed in the stimulating assembly, wherein the plurality of electrical stimulating contacts are configured to directly deliver electrical stimulation to the cochlea nerve cells.

11. A method, comprising:
receiving a sound signal via one or more sound input elements of a tissue-stimulating auditory prosthesis;
generating a plurality of drive signals based on the sound signal; and
delivering the drive signals to one or more stimulation coils positioned in proximity to a recipient's nerve cells to induce, via the one or more stimulation coils, current at the nerve cells that is representative of the sound signal.

12. The method of claim 11, wherein generating the plurality of drive signals comprises:
generating voltage signals for application to the one or more stimulation coils to induce current within the one or more stimulation coils.

13. The method of claim 11, wherein generating the plurality of drive signals comprises:
generating current signals for application to the one or more stimulation coils such that the current signals pass through the one or more stimulation coils.

14. The method of claim 11, wherein the stimulating assembly is a substantially flexible intra-cochlear stimulating assembly configured to be implanted into a cochlea of the recipient such that the one or more stimulation coils are adjacent to different populations of cochlea nerve cells.

15. The method of claim 11, wherein the generating the plurality of drive signals includes
extracting, from the sound signal, a plurality of channel magnitudes representing the strength of the sound signal in different frequency channels; and
utilizing the channel magnitudes to determine a level of current to be induced at populations of nerve cells associated with each frequency channel.

16. The method of claim 11, wherein the generating the plurality of drive signals includes
extracting, from the sound signal, a plurality of channel magnitudes representing the strength of the sound signal in different frequency channels; and
utilizing the channel magnitudes to determine a level of voltage to be induced at populations of nerve cells associated with each frequency channel.

17. The method of claim 11, further comprising:
concurrently delivering drive signals to a plurality of stimulation coils to cause the plurality of stimulation coils to concurrently induce current at the nerve cells.

18. The method of claim 11, further comprising:
inducing current at the nerve cells via at least one implanted extra-cochlear stimulation coil.

19. The method of claim 11, further comprising:
generating a plurality of electrical stimulation drive signals based on the sound signal; and
delivering the electrical stimulation drive signals to one or more electrical stimulation contacts positioned in proximity to a recipient's nerve cells to directly apply current to the nerve cells that is representative of the sound signal.

20. A hearing prosthesis, comprising:
a sound input element configured to receive a sound signal;
a coil drive unit configured to generate a plurality of drive signals based on the sound signal; and
a plurality of stimulation coils configured to induce, at nerve cells of a recipient, current based on the drive signals, wherein the current is configured to evoke perception of the sound signal by the recipient.

* * * * *